United States Patent
Santin

(10) Patent No.: US 11,098,367 B2
(45) Date of Patent: Aug. 24, 2021

(54) METHODS OF IDENTIFYING PATIENTS RESPONSIVE TO IMMUNOTHERAPEUTIC STRATEGIES

(71) Applicant: Yale University, New Haven, CT (US)

(72) Inventor: Alessandro Santin, Orange, CT (US)

(73) Assignee: Yale University, New Haven, CT (US)

( * ) Notice: Subject to any disclaimer, the term of this patent is extended or adjusted under 35 U.S.C. 154(b) by 266 days.

(21) Appl. No.: 15/113,339

(22) PCT Filed: Jan. 26, 2015

(86) PCT No.: PCT/US2015/012804
§ 371 (c)(1),
(2) Date: Jul. 21, 2016

(87) PCT Pub. No.: WO2015/112930
PCT Pub. Date: Jul. 30, 2015

(65) Prior Publication Data
US 2017/0002422 A1 Jan. 5, 2017

Related U.S. Application Data

(60) Provisional application No. 61/931,850, filed on Jan. 27, 2014.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/156* (2013.01)

(58) Field of Classification Search
None
See application file for complete search history.

(56) References Cited

PUBLICATIONS

Singh et al; Gastroenterology Report, vol. 3, pp. 289-297, 2015.*
Anguille et al; Lancet Oncol, vol. 15, 2014, p. e257-e267.*
International Search Report and Written Opinion for PCT International Application No. PCT/US2015/012804 dated Apr. 9, 2015.
Aboussekhra, et al., "Mammalian DNA nucleotide excision repair reconstituted with purified protein components", Cell 80(6), 1995, 859-868.
Albertson, et al., "DNA polymerase epsilon and delta proofreading suppress discrete mutator and cancer phenotypes in mice", Proc Natl Acad Sci U S A. 106(40), 2009, 17101-17104.
Bielas, et al., "Human cancers express a mutator phenotype", Proc Natl Acad Sci U S A. 103(48), 2006, 18238-18242.
Briggs, et al., "Germline and somatic polymerase ε and δ mutations define a new class of hypermiutated colorectal and endometrial cancers", J Pathol. 230(2), 2013, 148-153.

The Cancer Genome Atlas Research Network, "Integrated genomic characterization of endometrial carcinoma", Nature. 497(7447), 2013, 67-73.
Church, et al., "DNA polymerase ε and δ exonuclease domain mutations in endometrial cancer", Hum Mol Genet. 22(14), 2013, 2820-2828.
Edwards, et al., "*Saccharomyces cerevisiae* DNA polymerase epsilon and polymerase sigma interact physically and functionally, suggesting a role for polymerase epsilon in sister chromatid cohesion", Mol Cell Biol. 23(8), 2003, 2733-2748.
Fader, et al., "Early stage uterine serous carcinoma: management updates and genomic advances", Gynecol Oncol. 129(1), 2013, 244-250 (Abstract Only).
Greenman, et al., "Patterns of somatic mutation in human cancer genomes", Nature. 446(7132), 2007, 153-158.
Hampel, et al., "Screening for the Lynch syndrome (hereditary nonpolyposis colorectal cancer)", N Engl J Med. 352(18), 2005, 1851-1860.
Hussein, et al., "Clinicopathological analysis of endometrial carcinomas harboring somatic POLE exonuclease domain mutations", Mod Pathol. 28(4), 2015, 505-514.
Loeb, et al., "Human cancers express mutator phenotypes: origin, consequences and targeting", Nat Rev Cancer. 11(6), 2011, 450-457.
Meng, et al., "POLE exonuclease domain mutation predicts long progression-free survival in grade 3 endometrioid carcinoma of the endometrium", Gynecol Oncol. 134(1), 2014, 15-19 (Abstract Only).
Palles, et al., "Germline mutations affecting the proofreading domains of POLE and POLD1 predispose to colorectal adenomas and carcinomas", Nat Genet. 45(2), 2013, 136-144.
Piñol, et al., "Accuracy of revised Bethesda guidelines, microsatellite instability, and immunohistochemistry for the identification of patients with hereditary nonpolyposis colorectal cancer", JAMA. 293(16), 2005, 1986-1994.
Pogue-Geile, et al., "Defective mismatch repair and benefit from bevacizumab for colon cancer: findings from NSABP C-08", J Natl Cancer Inst. 105(13), 2013, 989-992.
Pospiech, et al., "DNA polymerase epsilon—more than a polymerase", Scientific World Journal. 3, 2003, 87-104.
Shinbrot, et al., "Abstract 114: Polymerase epsilon (POLE) mutations and mutator phenotypes in colorectal and endometrial tumors", Proceedings: AACR 104th Annual Meeting Apr. 6-10, 2013 <retrieved Mar. 12, 2015>, 2013 (Abstract Only).
Snyder et al., "Genetic basis for clinical response to CTLA-4 blockade in melanoma", N Engl J Med. 371(23), 2014, 2189-2199.
Yoshida, et al., "Concurrent genetic alterations in DNA polymerase proofreading and mismatch repair in human colorectal cancer", Eur J Hum Genet. Mar. 2011;19(3), 2011, 320-325.
Zhao, et al., "Landscape of somatic single-nucleotide and copy-number mutations in uterine serous carcinoma", Proc Natl Acad Sci U S A. 110(8), 2013, 2916-2921.

* cited by examiner

*Primary Examiner* — Jehanne S Sitton
(74) *Attorney, Agent, or Firm* — Saul Ewing Arnstein & Lehr LLP; Kathryn Doyle; Justin Crotty

(57) ABSTRACT

The invention includes a method of determining whether a mammal's cancerous tumor is associated with a hypermutator phenotype (i.e., harboring a large number of mutations) for the DNA Polymerase epsilon (POLE) gene as compared to normal cells. The invention further includes a method of selecting patients harboring an immunogenic tumor that is responsive to immunotherapy.

8 Claims, 15 Drawing Sheets

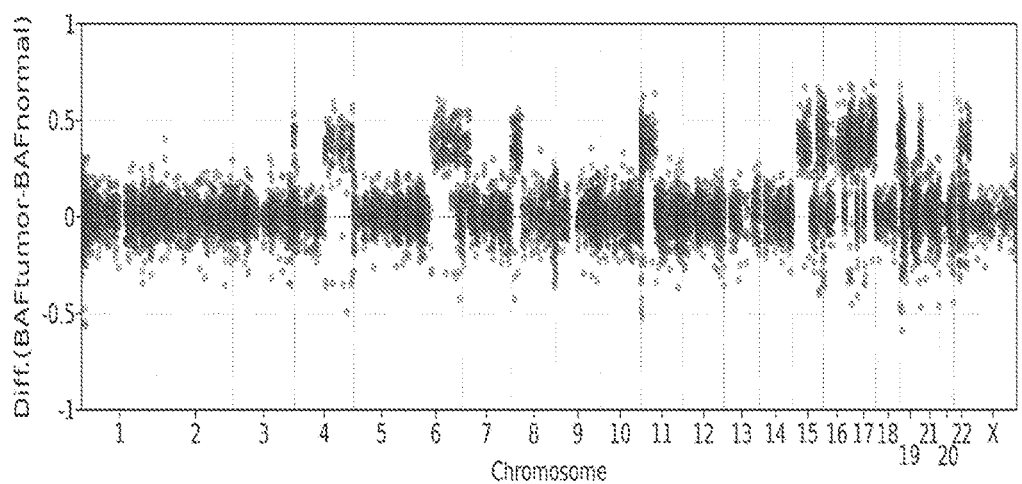
FIG. 6
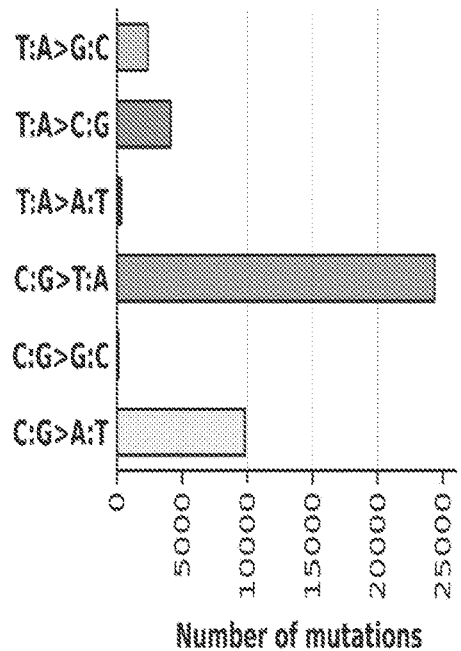 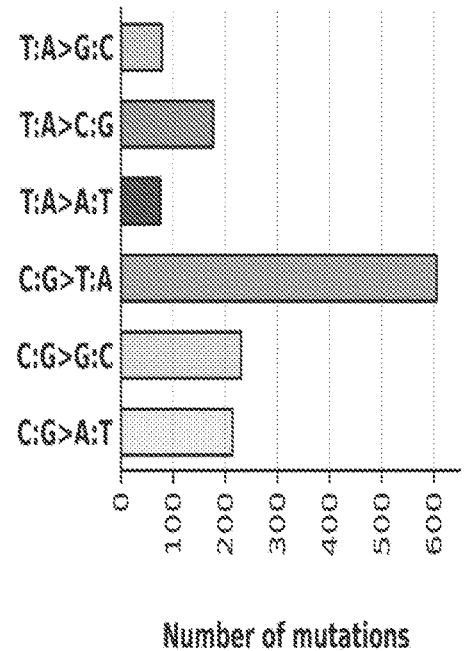
FIGS. 7A-7B

METHODS OF IDENTIFYING PATIENTS RESPONSIVE TO IMMUNOTHERAPEUTIC STRATEGIES

CROSS-REFERENCE TO RELATED APPLICATIONS

The present application is a 35 U.S.C. § 371 national phase application from, and claims priority to, International Application No. PCT/US2015/012804, filed Jan. 26, 2015, and published under PCT Article 21(2) in English, which claims priority under 35 U.S.C. § 119(e) to U.S. Provisional Patent Application No. 61/931,850, filed Jan. 27, 2014, which application is incorporated herein by reference in its entirety.

STATEMENT REGARDING FEDERALLY SPONSORED RESEARCH OR DEVELOPMENT

This invention was made with government support under CA122728, CA154460, CA176067, and CA016359 awarded by National Institutes of Health. The government has certain rights in the invention.

BACKGROUND OF THE INVENTION

Cancer, the uncontrolled growth of malignant cells, is a major health problem of the modern medical era and is one of the leading causes of death in developed countries. In the United States, approximately 40.8% of men and women will be diagnosed with a cancer at some point during their lifetime, and one in four deaths is caused by cancer (Jemal et al., CA Cancer J. Clin. 52:23-47 (2002); Howlader et al., SEER Cancer Statistics Review, 1975-2010, National Cancer Institute). The most-commonly identified human cancers include those that arise from organs and solid tissues, e.g., colon cancer, lung cancer, breast cancer, stomach cancer, prostate cancer, and endometrial cancer.

In the past decades remarkable advancements in cancer treatment arose particularly via therapies aiming on stimulating the immune system. Although immunotherapy could be highly efficacious, only small subsets of patients regardless of the organ of origin of the tumor are usually responsive to therapy. For example, in the pivotal Phase 3 trial conducted in previously treated patients with advanced melanoma, the overall response rate for the FDA-approved Ipilimumab antibody immunotherapy treatment was only 11% (Hodi et al., N Engl J Med. 363:211-223 (2010)). In addition, immunotherapy may be highly expensive, i.e., a single cycle of Ipilimumab immunotherapy costs about $120,000.

Early screening for some cancers, such as breast and colon cancer, can dramatically reduce their morbidity and mortality. In conjunction with the efforts in treating cancer, a variety of approaches have been applied to improve cancer diagnosis. Cancer behavior is highly heterogeneous. Certain types of tumors are generally diagnosed at an early stage, and typically have a good prognosis. In contrast, other types of tumors are difficult to diagnose and have a poor prognosis with a high chance of relapse and deaths (Bokhman, Gynecol Oncol 15(1): 10-17 (1983)). The poor prognosis motivates the determination of the molecular basis of tumors' aggressive behavior in hope of developing new effective treatment modalities.

A variety of investigations are underway to identify cancer genes. Procedures were developed that have allowed identification of genes causative of cellular transformation (Reddy et al., Nature 300, 149-152 (1982); Tabin et al. Nature 300, 143-149 (1982)), and complex processes such as invasiveness and metastasis (Douma et al. Nature. 430: 1034-9 (2004)). In vitro methods, using cellular or animal models, led to the discovery of dominant cancer genes, or oncogenes.

Many well-characterized cancer genes harbor somatic base substitutions or small insertions or deletions. For example, coding regions frame-shifts and point mutations account for 75% of the somatic mutations in the two major TP53 tumor suppressor genes (Olivier et al., Hum Mutat. 19:607-14 (2002); Stenson et al., Hum Mutat 21:577-81 (2003)). Large-scale sequencing approaches identified PI3K and some tyrosine phosphatases as somatically mutated in human colorectal cancer (Wang et al., Science 304:1164-6 (2004)). The B-raf oncogene, first described over 20 years ago, was recently shown to be mutated in human cancer (Garnett and Marais, Cancer Cell 16:313-319 (2004)). A number of efforts are currently underway to build integrated databases to enable sequence-based cancer genomics (Strausberg et al., Nat Rev Genet 4:409-418 (2003); Chin et al., Genes & Dev 25: 534-555 (2011); Simon and Roychowdhury, Nature Reviews Drug Discovery 12, 358-369 (2013)).

DNA polymerases (Pol) are essential for DNA replication and also play key roles in other processes within cells, including DNA repair, genetic recombination, reverse transcription, and the generation of antibody diversity via the specialized DNA polymerase, terminal deoxynucleotidyl transferase. Pol α (alpha), Pol δ (delta), and Pol ε (epsilon) are members of Family B Polymerases and are the main polymerases involved with nuclear DNA replication. Pol α complex starts replication then Pol ε and Pol δ take over the leading and lagging strand synthesis respectively.

DNA polymerase c (POLE) is an enzyme of both complex structure and function. While its main function is to extend the leading strand during replication, Pol ε's C-terminus is involved in the response to DNA damage, and could perform the gap-filling DNA repair synthesis (Aboussekhra et al., (1995) Cell 80, 859-868). It seems that this region mediates many of the functions of Pol ε, and it is this region, but not the Pol domain, that renders Pol ε indispensable for cell viability (Edwards et al., (2003) Mol. Cell. Biol. 23 (8): 2733-48; Pospiech et al., ScientificWorld Journal (2003)).

There is a great need in the art for the identification of patients harboring tumors that most likely would respond to immunotherapy. Furthermore, there is a need in the art for simple and low cost methods to determine whether patients with tumors harboring a "high mutator phenotype" related to POLE mutations would respond better to certain treatment modalities. The present invention satisfies these needs and may have major clinical and economic impacts.

BRIEF SUMMARY OF THE INVENTION

The invention includes a method for detecting or predicting whether a mammal with a cancerous tumor is responsive to immunotherapeutic treatment, wherein the method comprises comparing the nucleotide sequence of a DNA polymerase epsilon (POLE) gene from a sample isolated from the mammal's cancerous tumor and the nucleotide sequence of the corresponding from a control sample; wherein detection of one or more mutations in the POLE gene from the mammal's cancerous tumor indicates that the mammal carries a high mutator phenotype and, wherein, if the mammal carries a high mutator phenotype, the mammal is responsive to an immunotherapeutic treatment.

The invention also includes a method of treating a mammal with a cancerous tumor, wherein the method comprises comparing the nucleotide sequence of a DNA polymerase epsilon (POLE) gene from a sample isolated from the mammal's cancerous tumor and the nucleotide sequence of the corresponding from a control sample, wherein detection of one or more mutations in the POLE from the mammal's cancerous tumor indicates that the mammal carries a high mutator phenotype and, prescribing, if the mammal carries a high mutator phenotype, the administration of an immunotherapeutic treatment to the mammal.

The invention further includes a kit comprising a plurality of oligonucleotides that detect one or more mutations in a DNA polymerase epsilon (POLE) gene.

In certain embodiments, the mutation in the POLE gene from the mammal's cancerous tumor includes at least one selected from the group consisting of a base deletion, base insertion, base duplication, and base substitution. In yet other embodiments, the base mutation generates a synonymous or non-synonymous change in the corresponding protein or enzyme. In other embodiments, the protein or enzyme associated with the base mutation has distinct activity from the protein or enzyme from a control sample. In further embodiments, the cancerous tumor comprises at least one selected from the group consisting of lung, colon, breast, prostate, endometrial, ovarian, melanoma, kidney, liver, lymphoma and leukemia. In yet further embodiments, the detection of a high mutator phenotype in the mammal's cancerous tumor is indicative of a high immunogenicity in the mammal. In yet other embodiments, the immunotherapeutic treatment comprises a cytokine, an immune checkpoint blocker, a cancer vaccine, or a dendritic cell-based therapy. In yet other embodiments, the immunotherapeutic treatment comprises further administering to the mammal in need thereof an additional treatment selected from the group consisting of a chemotherapeutic treatment, an anti-cell proliferating treatment and any combination thereof. In other embodiments, the mammal is a human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A: Distribution of the number of protein-altering somatic mutations in 34 normal-tumor USC pairs. Subplot left, mutation spectrum in four hypermutator phenotype samples; subplot right, mutation spectrum in 30 moderately mutated samples. FIGS. 1B and 1C: Thirty tumors with moderate somatic burden are arranged by the total number of somatic point mutations from left to right. The four hypermutator phenotype tumors are excluded in this analysis. FIG. 1B: Significantly mutated genes are listed vertically by the order of damaging or conserved P values shown in Table 1. FIG. 1C: Genes with significant copy number variations (CNVs) and genes of interest are listed. Copy neutral status is shown as light grey rectangles. Crosses mark: five samples without CNV information.

FIG. 2A: Schematic representation of somatic mutations found in CHD4. The horizontal bar represents full-length CHD4 protein with functional domains shown as boxes. Somatic mutations found in USC are marked on top of the corresponding region (e.g. C464Y or E1628X). All mutations are missense mutations except E1628X, which is a nonsense mutation. FIG. 2B: C464 locates in the second PHD finger, which binds directly to histone H3 methylated at K9. An NMR structure of the second PHD domain of CHD4 has been determined [Protein Data Bank (PDB) ID: 2L75]. Large dark grey dot represents C464Y mutation. (Lower) A close-up view of the zinc-C464 interaction. FIG. 2C: Somatic mutations in catalytic core of CHD4 mapped to the crystal structure of a related protein, human CHD1 (sequence identity of the ATPase lobes is 42%, homology is 57% over 572 residues; PDB ID: 3MWY) (Hauk G, et al., Mol Cell 39(5): 711-723 (2010)): ATPase lobe 1; ATPase lobe 2; chromodomains and C-terminal bridge. Three mutations (large dark grey dots) in CHD4 fall within known conserved motifs (motifs B, V, VI) (Flaus A. et al., Nucleic Acids Res 34(10): 2887-2905 (2006)); three mutations were found in unknown helicase motif i, and two mutations were found in unknown motif ii. FIG. 2D: A close-up view of mutations in five motifs in FIG. 2C. Somatic mutations are labeled in light grey text (e.g. R957Q); amino acid positions in parentheses represent homologous positions in CHD1.

FIG. 3A: grey colored boxes represent functional domains in TAF1 with domain names noted below (Kloet et al., Mol Cell Biol 32(16): 3358-3369 (2012)). HAT domain, histone acetyltransferase domain. Mutations found in USC are marked at the top of the corresponding region (e.g. H612R). FIG. 3B: Multiple sequence alignment across vertebrate and invertebrate species around the seven mutations found in USC. Mutation positions in human TAF1 are labeled at the top. Sequence aligned by Clustal W2.0.

FIG. 6 is a graph that illustrates the loss of heterozygosity (LOH) from the FF-12 tumor-normal pair. Heterozygous single nucleotide polymorphism (SNP) locus from normal sample of FF-12 was extracted and the difference of B allele frequency (BAF) change in tumor sample is plotted along the genome. Regions with obvious shift in BAF change were called as LOH by manual curation. For example, chr4, 6, 7, 8, 11, 15, 16, 17, 19, 20, 22 all have LOH regions. Purity was estimated by averaged absolute BAF change in LOH regions multiplied by 2.

FIGS. 7A-7B are histograms that illustrate the mutation spectrum in USC and the numbers of base substitution in each of the 6 classes. FIG. 7A: Plot for 4 tumors with hypermutator phenotype. FIG. 7B: Plot for 30 moderately mutated tumors.

FIG. 9A: PP2A Holo-enzyme P179 and 5256 make up part of the A-B interface. Subunit A, subunit B, subunit C, recurrently mutated amino acids P179 and S256 and singletons are labeled. FIG. 9B: SV40 and subunit A SV40 virus binds regulatory subunit A with an overlapping site to the A-B interaction. Subunit A, SV40, recurrently mutated amino acids P179 and S256 and singletons are labeled.

DETAILED DESCRIPTION OF THE INVENTION

Figure 1A:
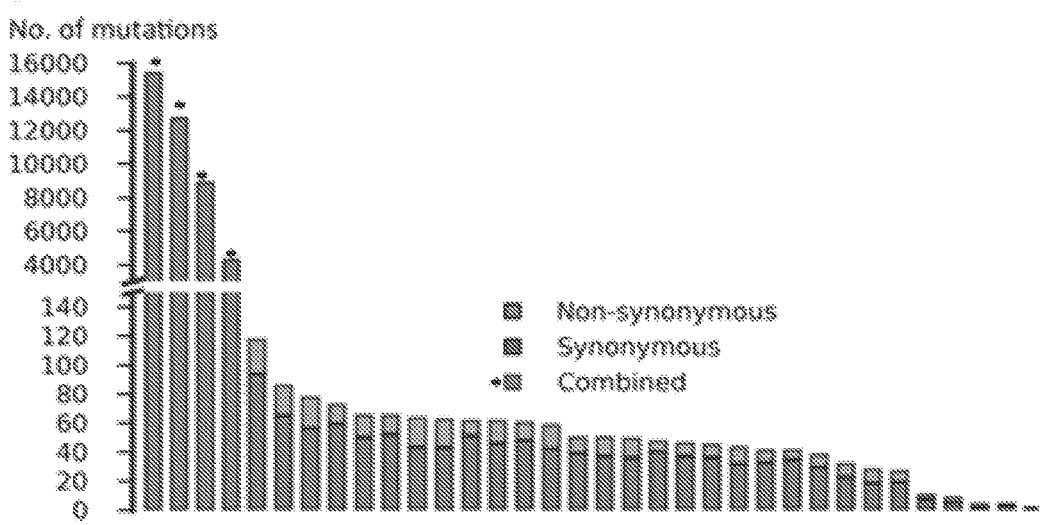
FIGS. 1A-1C are a series of graphs and figures that illustrate the finding that somatic variation pattern underlies uterine serous carcinoma (USC).

The invention relates to the unexpected discovery that in several types of cancer the DNA Polymerase epsilon (POLE) gene harbors one or more mutations as compared to normal cells. The invention further relates to a method for identifying patients with antigenic tumors highly sensitive to immunotherapy comprising identifying those patients carrying a POLE high mutator phenotype.

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

The term "biopsy" refers to a specimen obtained by removing tissue from a living patient for diagnostic examination.

A "subject" or "patient," as used therein, may be a human or non-human mammal. Non-human mammals include, for example, livestock and pets, such as ovine, bovine, porcine, canine, feline and murine mammals. Preferably, the subject is human.

A "mutation" as used therein is a change in a DNA sequence resulting in an alteration from its natural state. The mutation can comprise deletion and/or insertion and/or duplication and/or substitution of at least one desoxyribonucleic acid base such as a purine (adenine and/or thymine) and/or a pyrimidine (guanine and/or cytosine) Mutations may or may not produce discernible changes in the observable characteristics (phenotype) of an organism (subject).

The term "hypermutator phenotype" as used herein is defined as the large number of mutations found in a small subset of subject tumors.

The term "immunogenicity" as used herein is the ability of a particular substance, such as an antigen or epitope, to provoke an immune response in the body of a mammal. In one embodiment, this immune response is humoral and/or cell-mediated.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that may comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "RNA" as used herein is defined as ribonucleic acid.

The term the "immunotherapeutic agent" as used herein is meant to include any agent that activates the patient's immune system.

The term "therapeutic" as used herein means a treatment and/or prophylaxis. A therapeutic effect is obtained by suppression, remission, or eradication of a disease state.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease. This includes prevention of cancer.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2, 7, 3, 4, 5, 5.3, and 6. This applies regardless of the breadth of the range.

Description

Whole exome sequencing of a large cohort of uterine serous carcinoma (USC) has identified genes with increased numbers of somatic single-nucleotide and copy-number variants. Particularly, the sequencing data demonstrated that the distribution of the number of protein-altering somatic mutations deviated from a normal distribution. The majority of human tumors harbor a moderate number of somatic mutations (i.e., less than 100), while a consistent subset of human tumors originating from different tissues accumulate a much greater number of somatic mutations (>3000).

As demonstrated herein, the large number of mutations found in a small subset of human tumors defined as "hypermutator phenotype" were shown to be due to mutations taking place in DNA Polymerase and/or DNA mismatch repair genes. Particularly, patients diagnosed with a DNA Polymerase epsilon (POLE) hypermutator tumor phenotype were shown to experience an extraordinary better prognosis when compared to the remaining patients carrying a wild type POLE tumor phenotype. Sequencing of the POLE gene in hypermutator phenotype tumors revealed no germline mutations; however somatic mutations in this gene were highly prevalent in these tumors. Further investigations on POLE mutated human tumors have clarified that these tumors are characterized by: (1) high number of somatic mutations, (2) poorly differentiated histology, (3) resistance to chemotherapy, (4) high infiltration of tumor infiltrating lymphocytes (TIL), (5) high immunogenicity and (6) high sensitivity to immunotherapy.

Currently, microsatellite instability testing (MSI) and immunohistochemistry were both shown to be highly effective strategies for selecting patients for molecular genetic testing (germline mutation analysis) (Pinol et al., JAMA 293:1986-1994 (2005); Hampel et al., N Engl J Med 352: 1851-1860 (2005)). However, these current assays are not sufficiently sensitive to identify patients with tumors harboring a "high mutator phenotype" related to POLE mutations potentially responsive to immunotherapy. Without wishing to be limited by any theory, the sequencing method seems to be the ultimate choice.

Therefore, the identification, via sequencing, of POLE mutation in tumor tissues represents a novel and ideal method to select patients harboring highly immunogenic tumor highly responsive to immunotherapy. The results reported herein indicate that POLE mutation level may be exploited in the choice of using immunotherapy for treating cancer or other POLE related diseases.

Methods of the Invention

The invention includes a method of determining whether a cancerous tumor of mammal is associated with a hypermutator phenotype (i.e., harbors a large number of mutations) for the DNA Polymerase epsilon (POLE gene) as compared to normal cells. The invention further includes the use of this method as a novel way to select patients harboring highly immunogenic tumor that is responsive to immunotherapy.

In one aspect, the invention includes a method of detecting in a sample obtained from the mammal at least one mutation in the POLE gene that is capable of generating a high mutator phenotype. According to the methods, the diagnosis comprising sequencing the POLE gene.

In one embodiment, a mutation comprises deletion and/or insertion and/or duplication and/or substitution of at least one desoxyribonucleic acid base such as a purine (adenine and/or thymine) and/or a pyrimidine (guanine and/or cytosine) of the POLE DNA.

In one embodiment, a mutation comprises deletion and/or insertion and/or substitution of at least one amino acid of the POLE protein.

Any method known to those in the art can be employed for determining the mutation and/or hypermutation level of the gene of interest.

In one embodiment, the POLE gene is sequenced using a variety of DNA sequencing techniques that are well known to those of skill in the art (e.g. Sanger sequencing, Whole exome sequencing using next-generation sequencing). In another embodiment, the POLE gene expression is measure is a quantifying PCR (e.g. TaqMan®, Digital PCR).

In one embodiment, as demonstrated herein the nucleotide sequence and structure of POLE cancer gene is compared to the nucleotide sequence from a control sample. A nucleotide alteration of at least one cancer gene in the test sample relative to the control sample is indicative of the subject either having, or being at risk for developing, a cancer.

In a particular embodiment, the present invention is useful for detecting POLE high mutator phenotype in POLE related diseases, including but not limited to, cancer (such as lung, colon, breast, prostate, endometrial, ovarian, melanoma, kidney, liver, lymphomas and leukemias), HIV, immunologic deficiencies, retinal diseases and pathologic neovascularization diseases.

In one embodiment, as demonstrated herein, the detection of POLE, high mutator phenotype in a subject is indicative of a high immunogenicity in this subject and is indicative of a better prognosis when compared to subjects with a wild type POLE phenotype. In another embodiment, patients harboring an ultramutated tumor (i.e., POLE mutated, USC-FF40) develop strong proliferative responses in autologous CD4+ and CD8+ T cells when stimulated with autologous-monocyte derived dendritic cells loaded with USC lysate.

In one aspect, the detection of POLE high mutator phenotype in a subject is indicative of likelihood of positive response of this subject to immunotherapeutic treatment such as interleukin-2 and other cytokines, immune checkpoint blockers including but not limited to programmed cell death protein 1(PD-1) signaling (e.g. monoclonal antibodies that bind to PD-1), Ipilimumab and other blockers of cytotoxic T lymphocytes associated antigen A-4 (CTLA-4) signaling, cancer vaccines and dendritic cell-based therapies.

Kits

In certain embodiments, kits are provided. Commercially available kits for use in these methods are, in view of this specification, known to those of skill in the art. In general, kits will comprise a detection reagent that is suitable for detecting the presence of a polypeptide or nucleic acid, or mRNA of interest.

In other embodiments, there is a panel of probe sets. Preferred probe sets are designed to detect expression of one or more DNAs and provide information about the POLE high mutator phenotype in a cancerous tumor in a subject. Probe sets are particularly useful because they are smaller and cheaper than probe sets that are intended to detect as many DNAs (or mRNAs) as possible in a particular genome. The probe sets are targeted at the detection of DNAs that are informative about diagnosis or prediction of hypermutated genes in a cancerous tumor subject. Probe sets may also comprise a large or small number of probes that detect DNAs that are not informative on hypermutated genes in a cancerous tumor in a subject. Such probes are useful as controls and for normalization (e.g., spiked-in markers). Probe sets may be a dry mixture or a mixture in solution. In certain embodiments, probe sets can be affixed to a solid substrate to form an array of probes. It is anticipated that probe sets may also be useful for multiplex PCR. The probes may be nucleic acids (e.g., DNA, RNA, chemically modified forms of DNA and RNA), LNAs (Locked nucleic acids), or PNAs (Peptide nucleic acids), or any other polymeric compound capable of specifically interacting with the desired nucleic acid sequences.

It is contemplated that kits may be designed for isolating and/or detecting DNA or RNA in essentially any sample (e.g. blood, urine etc.), and a wide variety of reagents and methods are, in view of this specification, known in the art.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Materials and Methods

Investigation of the Landscape of Somatic Single-Nucleotide and Copy-Number Mutations in Uterine Serous Carcinoma (USC).

Patients and Specimens.

Fifty-seven patients with uterine serous carcinoma were studied. Their clinical features are presented in Table 2. DNA was purified and libraries were prepared. DNA and RNA fractions were isolated from the tissue using an All-Prep DNA/RNA mini kit (Qiagen) per the manufacturer's procedure. Genomic DNA was prepared from venous blood, primary fibroblast cultures or frozen myometrium by standard procedures. Light microscopic evaluation was performed on a hematoxylin and eosin stained section of each frozen tumor specimen submitted to sequencing for assessment of percent tumor nuclei and percent necrosis in addition to other pathology annotations. Each section was confirmed to contain a high purity of tumor epithelium (>60%) and minimal necrosis and used those sections for DNA extraction. Primary tumor cell lines purity was tested by morphology and by flow cytometry using pan-cytokeratin antibody staining (i.e., C-11-FITC, ab78478, Abcam Inc. Cambridge, Mass.). Only cell lines with tumor purity above 90% and less than 3 weeks of culture in vitro were used for sequencing.

Whole Exome Sequencing.

Genomic DNA was captured on the NimbleGen 2.1M human exome array and subjected to 74 base paired-end reads on the Illumina HiSeq instrument. Sequence reads were mapped to the reference genome (hg18) using the ELAND program. Reads outside the targeted sequences were discarded and statistics on coverage were collected from the remaining reads using perl scripts. ELAND was also used for indel detection. For matched normal-tumor pairs, somatic mutations were called by comparing reference and non-reference reads from the matched pair by Fisher's exact test with tumor-specific thresholds determined from approximation of the null distribution. For unmatched tumors, SAMtools was used to call variant bases appended with quality scores. Among these, common variants that are listed in public databases were excluded and only rare variants were considered as potential somatic variants. Identified variants were annotated based on novelty, impact on the encoded protein, conservation, and expression using an automated pipeline.

qRT-PCR.

RNA isolation from all primary USC cell lines was performed using TRIzol Reagent (Invitrogen, Carlsbad, Calif., USA), according to the manufacturer's instructions. Quantitative PCR was carried out with a 7500 RealTime PCR System using the manufacturer's recommended protocol (Applied Biosystems, Foster City, Calif., USA) to evaluate the expression of PIK3CA, PPP2R1A, FBXW7, HCFC1R1, CNTN4, LRRC7, MYO7B, MED12, TAF1, TTN, YIPF3, KRAS, CHD4, GRIN2A, ZEB2 and ATP1B4. The primers and probes were obtained from Applied Biosystems (i.e., FBXW7, Assay ID: Hs00217794_m1; CNTN4, Assay ID: Hs00330047_m1; HCFC1R1, Assay ID: Hs00372415_m1; TTN, Assay ID: Hs00399225_m1; TAF1, Assay ID: Hs00270322_m1; MED12, Assay ID: Hs00192801_m1; MYO7B, Assay ID: Hs00400099_m1; LRRC7, Assay ID: Hs00363532_m1; PIK3CA, Assay ID: Hs00180679_m1; PPP2R1A, Assay ID: Hs00204426_m1; YIPF3, Assay ID: Hs00209862_m1; KRAS, Assay ID: Hs00270666_m1; CHD4, Assay ID: Hs00172349_m1; GRIN2A, Assay ID: Hs00168219_m1; ZEB2, Assay ID: Hs00207691_m1; TP53, Assay ID: Hs01034249_m1ATP1B4, Assay ID: Hs00201320_m1). The comparative threshold cycle method was used to determine gene expression in each sample, relative to the value observed in non-malignant endometrial epithelial cell samples collected from similar age women, using glyceraldehyde-3-phosphate dehydrogenase (Assay ID Hs99999905 ml) RNA as an internal control.

Investigation of the Prognosis and the Immunogenicity of Polymerase Epsilon Mutations in Uterine Serous Carcinoma (USC)

Patients and Specimens

Tumor tissue and peripheral blood lymphocytes (PBL) were obtained from a total of 10 patients (5 harboring tumors with POLE mutations and 5 harboring tumors with wild type POLE). Specimens were obtained at the time of surgery through the Gynecologic Oncology Section of the Obstetrics and Gynecology Department and the Pathology Department at the University of Arkansas for Medical Sciences (UAMS), Little Rock, Ark., and at Yale University School of Medicine under approval of the Institutional Review Board. Patients did not receive any form of therapy prior to surgery. Patient characteristics and molecular features of tumors included in the study are found in Table 8. With the exception of UTE4 and UTE9, two endometrial endometrioid carcinomas found to harbor POLE mutations by standard Sanger sequencing, (Table 8), the remaining tumor samples had previously undergone whole exome sequencing (Zhao et al., Proc Natl Acad Sci USA 110(8):2916-21 (2013)). For UTE4 and UTE9, primer sets that cover the exonuclease domain regions (where mutations were previously identified in endometrial cancer) of POLE were used to amplify exonuclease domain genomic regions prior to Sanger sequencing, as previously described (Meng et al., Gyn. Onc. 134: 15-19 (2014)).

Tumor Cell Lines

Fresh endometrial tumor cells were obtained from surgical specimens. Single cell suspensions were obtained by processing solid tumor samples under sterile conditions at room temperature as previously described (Santin et al., Br J Cancer 7; 86(1): 151-157 (2002)). Briefly, viable tumor tissue was mechanically minced in RPMI 1640 to portions no larger than 1-3 mm$^3$ and washed twice with RPMI 1640. The portions of minced tumor were then placed into 250 ml trypsinizing flasks containing 30 ml of enzyme solution [0.14% collagenase Type I (Sigma, St. Louis, Mo.) and 0.01% DNAse (Sigma, 2000 KU/mg)] in RPMI 1640, and incubated on a magnetic stirring apparatus overnight at 4° C. Enzymatically dissociated tumor was then filtered through 150 μm nylon mesh to generate a single cell suspension. The resultant cell suspension was then washed twice in RPMI 1640 plus 10% autologous plasma. Fresh tumor cell lines were maintained initially in RPMI 1640, supplemented with 10% FBS at 37° C., 5% $CO_2$. All experiments were performed with fresh or cryopreserved tumor cultures which had at least 90% viability and contained >99% tumor cells.

Preparation of Tumor Lysate $5\times10^6$ to $10\times10^6$ autologous USC/tumor cells, harvested by scraping (or equivalent amount of protein tumor material obtained from fresh frozen tumor specimens), were washed twice with phosphate-buffered saline (PBS, pH7.4) and lysed by three to four freeze cycles (in liquid nitrogen) and thaw cycles (room temperature). Lysis was monitored by light microscopy. Larger particles were removed by centrifugation (10 min, 600 rpm/400 g), supernatants were passed through a 0.2-μm filter, and stored at −80° C. until use.

Isolation of Peripheral Blood Lymphocytes (PBL) and Generation of Dendritic Cells (DC).

PBL were separated from heparinized venous blood by Ficoll-Hypaque (Sigma) density gradient centrifugation and either cryopreserved in RPMI 1640 (Gibco-BRL) plus 10% DMSO and 30% autologous plasma, or immediately used for DC generation. Briefly, PBL obtained from 20-42 ml of peripheral blood were placed into 6-well culture plates (Costar, Cambridge, Mass., USA) in AIM-V medium (Gibco-BRL) at 0.5-1×10$^7$/3 ml per well. After 2 h at 37° C., nonadherent cells were removed, and the adherent cells were cultured at 37° C. in a humidified 5% CO2/95% air incubator, in medium supplemented with recombinant human GM-CSF ((800 Uml/1), Immunex, Seattle, Wash., USA) and IL-4 ((1000 U ml−1) Genzyme, Cambridge, USA). Every 2 days, 1 ml of spent medium was replaced by 1.5 ml of fresh medium containing 1600 Uml−1 GM-CSF and 1000 Uml−1 IL-4, to yield final concentrations of 800 Um/−1 and 500 Uml/1, respectively. After 6 or 7 days of culture, DC were harvested for pulsing with tumor lysate as described below. The DC purity (i.e. cells strongly expressing HLA-DR+, CD86+, CD40+, and CD14−) ranged from 58 to 86% of the total cell population with a mean of 69±12%, as previously characterized by Santin A. D. and colleagues (Santin A. D. et al., Br J Cancer 7; 86(1): 151-157 (2002)).

Dendritic Cells (DC) Pulsing

Following culture, DC were washed twice in AIM-V and added to 50 ml polypropylene tubes (Falcon, Oxnard, Calif., USA). The cationic lipid DOTAP (Boehringer Mannheim, Indianapolis, Ind., USA) was used to deliver the total cell extract into cells. Five hundred microliters of total cell extract derived from 5-10×10$^6$ tumor cells in AIM-V and DOTAP (125 μg in 500 μl of AIM-V) were mixed in 12×75 mm polystyrene tubes at room temperature for 20 min. The complex was added to the DC in a total volume of 2-5 ml of AIM-V and incubated at 37° C. with occasional agitation for 3 h. The cells were washed twice with PBS and resuspended in AIM-V as described below.

USC-Lysate-Pulsed Autologous DC Proliferation of CD4 and CD8+ T Cells In Vitro

Fresh or cryopreserved responder PBL were washed and resuspended in AIM-V culture medium at 10-20×10$^6$ cells per well in 6-well culture plates (Costar) with tumor lysate-pulsed autologous DC (ratios from 20:1 to 30:1 responder PBL: DC). At day 5, PBL were collected and CD4+ and CD8+ T cell proliferations were counted using flow cytometric techniques (i.e., CFSE assays analyzed on a FACScan Becton Dickinson). The cultures were supplemented with recombinant human IL-2 (10 U/ml Aldesleukin, Chiron Therapeutics, Emeryville, Calif.) and incubated at 37° C. Human rIL-2 (10 U/ml) was added to the cultures thereafter every 4 days. At day 21, CD8+ cells were separated from the bulk cultures by positive selection with CD8-Dynabeads (Dynal Inc., Lake Success, N.Y.) before being assayed for Cytotoxic T Lymphocyte (CTL) activity. Autologous lymphoblasts were prepared by 3-day stimulation with PHA (GIBCO-BRL, 1 mg/ml) in RPMI-1640 plus IL-2 (25 U/ml) as negative control targets. EBV-transformed autologous lymphoblastoid B-cell lines (LCL) were established by coculture of PBMCs with EBV-containing supernatant from the B95.8 cell line in the presence of 1 mg/ml cyclosporin A (Sandoz, Camberley, UK) and were maintained in AIM-V supplemented with 10% human AB serum (Gemini Bioproducts).

T-Cell Proliferation Assay

CD4+ T cells, derived from day 21 CD8+ depleted T cell populations were restimulated once with tumor lysate-pulsed DC at a 20:1 ratio, and 2-3 weeks later further purified by positive selection with CD4-Dynabeads (Dynal Inc. Lake Success, N.Y.) to obtain a population more than 99% pure. Lymphoproliferative responses were tested using autologous DC and/or LCL pulsed with tumor lysate from POLE mutated vs POLE wild type tumors. Briefly tumor lysate-pulsed or control PHA-activated peripheral blood lymphocytes lysate-pulsed or unpulsed autologous DC or LCL were seeded in a 96 well/plates (2×10$^4$ cell/well). CD4+ T cells (2×10$^4$ cell/well) were tested for specific proliferation after 72 h. Cultures were pulsed with 1 mCi/well of [3H] thymidine for the last 16 h, and incorporated radioactivity was measured as described (Santin et al., Journal of Virology 1999; 73(7):5402-5410). All assays were carried out in triplicate wells. In additional experiments, tumor-lysate stimulated CD4+ T cells or unstimulated PBL from POLE mutated vs POLE wild type patients were stained with carboxyfluorescein succinimidyl ester (CFSE) (CellTrace CFSE Cell Proliferation Kit, Invitrogen, Carlsbad, Calif.) at a working concentration of 10 micromolar as previously described (English et al., Cancer. 2014 Sep. 23) in the absence of IL2. The CFSE labeled cells were plated and cultured in the presence of tumor lysate-pulsed or PHA-activated peripheral blood lymphocytes lysate-pulsed autologous DC or LCL for 5 to 6 days. Cells were collected and labeled with CD8 and CD4 (Becton Dickinson) and analyzed on a flow cytometer (FacsCalibur, Becton Dikinson) using Sciquest. The percentage and numbers of CD8+ and CD4+ T cells in the control PHA-activated peripheral blood lymphocytes lysate-pulsed autologous DC vs tumor lysate-pulsed DC treated wells were calculated after analysis by flow cytometry to determine CD8+ and CD4+ T cell proliferation induced in this co-culture system.

Cytotoxic Activity

A standard 4-hour chromium ($^{51}Cr$) release assay was performed to measure the cytotoxic reactivity of DC-tumor lysate stimulated CD8+ T lymphocytes. PHA-activated peripheral blood lymphocytes and/or EBV-transformed LCL were used as autologous control targets. The percentage cytotoxicity was calculated by the following formula: % cytotoxicity=100×[(E−S)/T−S)], where E is the experimental release, S is the spontaneous release by effector cells, T is the maximum release by target cells lysed with 1% SDS.

Flow Cytometric Analysis of Intracellular Cytokines

Flow cytometric analysis of intracellular cytokine expression in CD4+ and CD8+ T cells were tested at about 4-6 weeks after priming, after resting for 14 days after the last antigen stimulation prior to activation with autologous DC pulsed with PHA-activated peripheral blood lymphocytes or tumor lysate from POLE mutated vs POLE wild type tumors. OKT3-stimulated T cells were used as positive controls in all the experiments. Briefly, T cells ($5 \times 10^5$/ml) were incubated at 37° C. for 12 h in AIM-V plus 5% autologous plasma with PHA-activated peripheral blood lymphocytes or tumor lysate pulsed DC (30:1 T cell to DC ratio) and 10 µg/ml Brefeldin A. The cells were harvested, washed and fixed with 2% paraformaldehyde in PBS for 20 min at room temperature, after which they were washed and stored overnight in PBS at 4° C. For intracellular staining, the cells were washed and permeabilized by incubation in PBS plus 1% BSA and 0.5% saponin (S-7900, Sigma) for 10 min at room temperature. Activated and control cells were stained with FITC-anti-IFN-γ, and PE-anti-IL-4, and isotype-matched controls (FITC-anti-Igg2a and PE-anti-Igg1) from Becton-Dickinson. After staining, cells were washed twice with PBS plus 0.5% BSA. Analysis was conducted on a flow cytometer (FacsCalibur, Becton Dikinson) using Sciquest.

Statistics

Student t-test was used to evaluate differences in cytotoxic activity, cytokine secretion and proliferation by CD8+ T cells and CD8+ and CD4+DC-stimulated T cells, respectively. Statistical analysis was performed using SPSS version 18. A P-value of <0.05 was considered as the level of statistical significance.

Tables

Table 1: Genes with Significant Mutation Burden in 52 USC. Recurrent (no.), positions with recurrent mutations (no. of instances); Cons MS, missense mutations at conserved positions; Dam+Cons, damaging+conserved missense mutations.

Table 2: Clinical Features of Uterine Serous Carcinoma Patients.
[1] Race information comes from PCA analysis. A, African; E, European; H, Hispanic.
[2] The staging used in the table is the 1988 FIGO (International Federation of Gynaecology and Obstetrics) staging system. *REC denotes that recurrent tumor was sequenced.
[3] For uniformity with the current literature the World Health Organization guidelines for epithelial tumors (i.e., USC that contain <10% of a second malignant component are considered 'pure' USC) was used.
[4] Chemotherapy "yes" means that the tumor biopsy sequenced was collected after the patient had received chemotherapy (i.e., carboplatin and paclitaxel).

Table 3: Exome Run Quality Summary for all Samples.

Table 4: Mismatch Repair Gene Mutations and POLE Mutations in Hypermutated Samples.

Underlined mutations highlight damaging mutations and recurrent mutations. *Fisher p-value, showing likelihood of the somatic calls being real.

Most of cases, $p=10^{-4}$ is the cutoff value. For calls from unmatched samples, quality scores from Samtools are given since Fisher p-values are not available for these cases **LOH, loss of heterozygosity Table 5: Significantly duplicated intervals.
* Gene names listed if gene number less than 50. Otherwise, gene names can be accessed using the coordinates provided in the table via portals such as the UCSC genome browser (http://genome.ucsc.edu/cgi-bin/hgGateway). ** Cancer gene: COSMIC cancer census gene Table 6: Significantly Deleted Intervals.
* Gene names listed if gene number less than 50. Otherwise, gene names can be accessed using the coordinates provided in the table via portals such as the UCSC genome browser (http://genome.ucsc.edu/cgi-bin/hgGateway). ** Cancer gene: COSMIC cancer census gene Table 7: Comparison with High-Grade Ovarian Serous Carcinoma (HGS-OvCa)
^ Significantly mutated genes in USC; #Significantly mutated genes in HGS-OvCa Table 8: Patient Characteristics and Molecular Features of Tumors.

TABLE 1

Genes with significant mutation burden in 52 USC.

| Gene | Recurrent (no.) | Coding length (bp) | No. non-synonymous mutations | Non-synonymous P value | No. damaging mutations | No. Cons MS | Dam + Cons P value | No. silent mutations |
|---|---|---|---|---|---|---|---|---|
| TP53 | R43 (2), C44 (2), R116 (4), G134 (3), R141 (2) | 1,222 | 30 | 1.34E−75 | 3 | 14 | 1.01E−45 | 0 |
| PIK3CA | E542 (3), N1044 (2) | 3,287 | 13 | 6.39E−23 | 0 | 13 | 4.26E−27 | 0 |
| CHD4 | F1112 (2) | 5,895 | 11 | 3.82E−17 | 1 | 10 | 1.05E−20 | 0 |
| FBXW7 | R465 (4) | 2,168 | 9 | 1.05E−17 | 0 | 9 | 1.08E−20 | 1 |
| PPP2R1A | P179 (4), S256 (2) | 1,830 | 8 | 1.28E−16 | 0 | 8 | 2.60E−19 | 0 |
| TAF1 | — | 5,834 | 7 | 2.71E−10 | 0 | 7 | 1.19E−12 | 0 |
| KRAS | G12 (2) | 586 | 3 | 2.61E−08 | 0 | 3 | 1.66E−09 | 0 |
| PTEN | — | 1,248 | 3 | 2.28E−07 | 1 | 2 | 1.46E−08 | 0 |
| HCFC1R1 | — | 433 | 2 | 8.00E−07 | 0 | 2 | 1.01E−07 | 0 |
| CDKN1A | — | 503 | 2 | 1.25E−06 | 0 | 2 | 1.58E−07 | 0 |
| CTDSPL | — | 863 | 2 | 7.86E−06 | 0 | 2 | 9.99E−07 | 0 |
| YIPF3 | — | 1,089 | 2 | 1.25E−05 | 0 | 2 | 1.59E−06 | 0 |
| SPOP | — | 1,161 | 2 | 1.51E−05 | 0 | 2 | 1.92E−06 | 0 |
| FAM132A | — | 941 | 2 | 1.51E−05 | 0 | 2 | 1.93E−06 | 0 |

Example 1

Exome Sequencing of USC.

Fifty-seven patients with uterine serous carcinoma were studied. Their clinical features are presented in Table 2.

TABLE 2

Clinical features of uterine serous carcinoma patients

| PairID/SampleID | Sample type | Status | Age | Ethinicity[1] | Stage[2] | Histology[3] | Chemo-therapy[4] |
|---|---|---|---|---|---|---|---|
| ARK-15N | Cell line | Matched | 67 | E | IIIC | PURE | YES |
| ARK-17 | Cell line | Matched | 59 | E | IIIA | PURE | NO |
| ARK-18 | Cell line | Matched | 62 | A | IIB | PURE | NO |
| ARK-19 | Cell line | Matched | 65 | E | IA | PURE | YES |
| ARK1 | Cell line | Matched | 62 | A | IVA | PURE | NO |
| ARK11 | Cell line | Matched | 80 | A | IIIC | MIXED | NO |
| ARK13N | Cell line | Matched | 67 | E | IVB | MIXED | YES |
| ARK2 | Cell line | Matched | 63 | A | IVB | PURE | NO |
| ARK6 | Cell line | Matched | 48 | E | IB | MIXED | NO |
| ARK7 | Cell line | Matched | 75 | E | IIC | PURE | NO |
| ARK8 | Cell line | Matched | 88 | E | IIIA | PURE | NO |
| ARK9 | Cell line | Matched | 73 | A | IIIC | MIXED | NO |
| FF-1 | Fresh frozen tissue | Matched | 67 | E | IIIC | PURE | NO |
| FF-10 | Fresh frozen tissue | Matched | 69 | E | IVA | PURE | NO |
| FF-11 | Fresh frozen tissue | Matched | 58 | A | IA | MIXED | NO |
| FF-12 | Fresh frozen tissue | Matched | 80 | E | IIB | MIXED | NO |
| FF-13 | Fresh frozen tissue | Matched | 75 | E | IIC | PURE | NO |
| FF-14 | Fresh frozen tissue | Matched | 59 | E | REC* | PURE | YES |
| FF-16 | Fresh frozen tissue | Matched | 54 | E | IIIC | MIXED | NO |
| FF-17 | Fresh frozen tissue | Matched | 73 | A | IVB | PURE | NO |
| FF-19 | Fresh frozen tissue | Matched | 74 | E | IVB | PURE | NO |
| FF-2 | Fresh frozen tissue | Matched | 36 | A | IB | PURE | NO |
| FF-3 | Fresh frozen tissue | Matched | 78 | E | IC | PURE | NO |
| FF-35 | Fresh frozen tissue | Matched | 63 | A | IVB | PURE | NO |
| FF-4 | Fresh frozen tissue | Matched | 64 | E | IB | PURE | NO |
| FF-40 | Fresh frozen tissue | Matched | 57 | E | IB | PURE | NO |
| FF-41 | Fresh frozen tissue | Matched | 65 | E | IA | PURE | NO |
| FF-42 | Fresh frozen tissue | Matched | 71 | H | IA | PURE | YES |
| FF-43 | Fresh frozen tissue | Matched | 67 | E | IIIC | PURE | NO |
| FF-5 | Fresh frozen tissue | Matched | 66 | A | IB | MIXED | NO |
| FF-6 | Fresh frozen tissue | Matched | 63 | A | IA | PURE | NO |
| FF-7 | Fresh frozen tissue | Matched | 49 | A | IVA | PURE | NO |
| FF-8 | Fresh frozen tissue | Matched | 66 | A | IVB | PURE | NO |
| FF-9 | Fresh frozen tissue | Matched | 56 | E | IIIC | MIXED | NO |
| USC-FF-18 | Fresh frozen tissue | Unmatched | 72 | E | IIIC | PURE | NO |
| USC-FF-20 | Fresh frozen tissue | Unmatched | 65 | E | IIC | PURE | NO |
| USC-FF-21 | Fresh frozen tissue | Unmatched | 70 | A | IIIA | PURE | NO |
| USC-FF-22 | Fresh frozen tissue | Unmatched | 73 | A | IIB | PURE | NO |
| USC-FF-23 | Fresh frozen tissue | Unmatched | 60 | E | IB | MIXED | NO |
| USC-FF-24 | Fresh frozen tissue | Unmatched | 60 | E | IIIA | MIXED | NO |
| USC-FF-25 | Fresh frozen tissue | Unmatched | 76 | A | IVB | PURE | NO |
| USC-FF-26 | Fresh frozen tissue | Unmatched | 76 | A | IIIC | PURE | NO |
| USC-FF-27 | Fresh frozen tissue | Unmatched | 57 | E | IIC | PURE | NO |
| USC-FF-28 | Fresh frozen tissue | Unmatched | 71 | E | IIIA | PURE | NO |
| USC-FF-29 | Fresh frozen tissue | Unmatched | 70 | A | IB | PURE | NO |
| USC-FF-30 | Fresh frozen tissue | Unmatched | 77 | E | IIIA | MIXED | NO |
| USC-FF-31 | Fresh frozen tissue | Unmatched | 70 | E | IIA | PURE | NO |
| USC-FF-32 | Fresh frozen tissue | Unmatched | 75 | E | IIIC | PURE | YES |
| USC-FF-33 | Fresh frozen tissue | Unmatched | 66 | A | IIIC | PURE | YES |
| USC-FF-34 | Fresh frozen tissue | Unmatched | 62 | E | IA | PURE | NO |
| USC-FF-36 | Fresh frozen tissue | Unmatched | 55 | A | IIB | PURE | NO |
| USC-FF-37 | Fresh frozen tissue | Unmatched | 74 | H | IIIC | PURE | YES |
| USC-FF-38 | Fresh frozen tissue | Unmatched | 76 | E | IIIC | PURE | NO |
| USC-FF-39 | Fresh frozen tissue | Unmatched | 81 | A | IVB | PURE | NO |
| USPC-ARK-20 | Cell line | Unmatched | 42 | E | IIB | PURE | NO |
| USPC-ARK10 | Cell line | Unmatched | 79 | E | IVB | PURE | NO |
| USPC-ARK4 | Cell line | Unmatched | 82 | E | IVB | PURE | NO |

Upon surgical removal of tumors, primary cell lines were prepared (15 tumors) or tumors were frozen (42 tumors). Exome sequencing was performed on all tumors; for 34 of these, DNA samples from normal tissue were available and sequenced. Exome sequencing was performed using the NimbleGen/Roche capture reagent followed by 74 base paired-end DNA sequencing on the Illumina HiSeq platform (Choi et al., Proc Natl Acad Sci USA 106(45): 19096-19101 (2009)). By design, tumor samples were sequenced to greater depth of coverage to permit detection of somatic mutations in tumors despite admixture of normal and tumor cells in these samples. For tumors and normal DNA, each targeted base was sequenced by a mean of 187 and 100 independent reads, respectively (Table 3 below).

TABLE 3

Exome run quality summary for all samples.

| Sample origin | Matched | | Unmatched |
|---|---|---|---|
| | Normal | Tumor | Tumor |
| Number | 34 | 34 | 23 |
| Status | Normal | Tumor | Tumor |
| Lanes used | 1/3 | 2/3 | 2/3 |
| Single end/Paired ends | PE | PE | PE |
| Read length | 74 bp | 74 bp | 74 bp |
| # of reads per lane (M) | 89 | 188 | 175 |
| Median coverage (X) | 84 | 165 | 144 |
| Mean coverage (X) | 100 | 199 | 170 |
| % on genome | 92.33% | 92.21% | 92.60% |
| % on target | 73.43% | 68.98% | 62.76% |
| % of bases covered at least 4x | 97.16% | 97.93% | 97.78% |
| % of bases covered at least 8x | 95.63% | 97.06% | 96.89% |
| % of bases covered at least 20x | 90.33% | 94.66% | 94.20% |
| Mean error rate | 0.42% | 0.49% | 0.47% |
| % of PCR duplicate | 4.95% | 9.98% | 7.63% |

Of all targeted bases in tumors, 94.5% were read by 20 or more independent reads; mean per-base per read error rates were 0.42% for normal DNA and 0.48% for tumor DNA. Segments of loss of heterozygosity (LOH) were called from the difference in B-allele frequency between tumor-normal pairs (FIG. 6), allowing estimates of tumor purity, which were above 60% for frozen tumors and higher for primary cell lines. Somatic mutations were identified by the variant reads in tumors that were significantly more frequent than expected by chance. At the coverage levels studied, there was no significant relationship between tumor purity and the number of somatic variants detected, consistent with sufficient depth of coverage having been achieved to identify the vast majority of somatic mutations. Variants in genes implicated in the pathogenesis of USC were verified by direct Sanger sequencing and were found to be expressed in all available USC cell lines.

Example 2

Tumors with Hypermutator Phenotype.

The number of protein-altering somatic mutations per tumor markedly deviated from a normal distribution (FIG. 1A). In the discovery set of 34 USC with matched normal DNA, 30 tumors had fewer than 100 protein-altering somatic mutations (median 36), whereas 4 had more than 3,000 somatic mutations each. Only one of these tumors was from a cell line (with limited propagation), and none came from patients who had received chemotherapy before sample acquisition. These tumors with high mutation burden were also notable for having no LOH segments or copy-number variants (CNVs), a feature found in only five other tumors. These features suggest a hypermutator phenotype due to deficiency of mismatch repair (MMR) or polymerase 6 (POLE) genes (Loeb et al., Nat Rev Cancer 11(6):450-457 (2011); Yoshida et al., Eur J Hum Genet 19(3): 20-325 (2011)). Consistent with this, these hyper-mutated tumors showed a paucity of T:A>A:T or C:G>A:T transversions (FIG. 7) (Greenman et al., Nature 446(7132):153-158 (2007)). Examination of the POLE and MMR genes showed no germ-line mutations; however, somatic mutations in these genes were highly prevalent in these tumors (mean of 4 per tumor, including 4 premature termination mutations for MMR genes and a mean of 4.5 per tumor for POLE) and more frequent than expected by chance ($P=2.23\times10^{-3}$) (Table 4 below).

TABLE 4

Mismatch repair gene mutations and POLE mutations in hypermutated Samples.

| Sample | Matched/ unmatched | Gene | Status | AA change | AA location/ protein length | P-value/ QS* | LOH** |
|---|---|---|---|---|---|---|---|
| ARK6T | Matched | MLH1 | Missense | E89D | 89/756 | 1.23E−29 | no |
| | | MLH1 | Missense | P705S | 705/756 | 3.05E−18 | no |
| | | MLH3 | Missense | A1246T | 1246/1453 | 7.30E−16 | no |
| | | MSH6 | Nonsense | E1322X | 1322/1360 | 8.68E−11 | no |
| | | POLE | Missense | C1642Y | 1642/2286 | 4.74E−06 | no |
| | | POLE | Missense | A1967V | 1967/2286 | 2.98E−65 | no |
| | | POLE | Missense | G2076V | 2076/2286 | 9.83E−12 | no |
| | | POLE | Missense | L2207I | 2207/2286 | 1.11E−11 | no |
| | | POLE | Missense | D368Y | 368/2286 | 3.19E−25 | no |
| | | POLE | Missense | H67N | 67/2286 | 7.44E−25 | no |
| | | POLE | Missense | A832T | 832/2286 | 1.28E−07 | no |
| FF-4T | Matched | MLH3 | Nonsense | E1288X | 1288/1453 | 1.72E−09 | no |
| | | MSH2 | Nonsense | E580X | 580/934 | 4.34E−07 | no |
| | | M6H3 | Missense | A396T | 396/1137 | 3.88E−07 | no |
| | | PMS1 | Missense | R93C | 93/932 | 2.68E−10 | no |
| | | PMS2 | Missense | L266I | 266/862 | 1.24E−07 | no |
| | | POLE | Missense | M295R | 295/2286 | 2.32E−08 | no |
| FF-9T | Matched | MLH3 | Missense | P1178H | 1178/1453 | 2.66E−15 | no |
| | | MSH2 | Nonsense | R680X | 680/934 | 5.71E−23 | no |
| | | MSH2 | Missense | E749A | 749/934 | 1.65E−16 | no |
| | | MSH3 | Missense | Y1011H | 1011/1137 | 2.22E−24 | no |
| | | MSH6 | Missense | A1055T | 1055/1360 | 1.78E−06 | no |
| | | PMS1 | Missense | L252R | 252/932 | 6.13E−15 | no |
| | | POLE | Missense | T1052M | 1052/2286 | 1.08E−05 | no |
| | | POLE | Missense | V1452A | 1452/2286 | 9.36E−17 | no |
| | | POLE | Missense | V411L | 411/2286 | 7.41E−11 | no |
| | | POLE | Missense | R742C | 742/2286 | 6.04E−23 | no |
| | | POLE | Missense | R77C | 77/2286 | 4.76E−22 | no |
| FF-40T | Matched | MSH2 | Missense | D91Y | 91/934 | 3.45E−05 | no |
| | | POLE | Missense | F1099S | 1099/2286 | 8.74E−05 | no |
| | | POLE | Missense | F1672L | 1672/2286 | 3.55E−23 | no |
| | | POLE | Missense | V411L | 411/2286 | 5.98E−15 | no |
| | | POLE | Missense | Y470H | 470/2286 | 2.21E−32 | no |
| | | POLE | Missense | S928I | 928/2286 | 6.23E−29 | no |

TABLE 4-continued

Mismatch repair gene mutations and POLE mutations in hypermutated Samples.

| Sample | Matched/ unmatched | Gene | Status | AA change | AA location/ protein length | P-value/ QS* | LOH** |
|---|---|---|---|---|---|---|---|
| FF-24 | Unmatched | MLH1 | Missense | L585F | 585/756 | 228 | no |
| | | MSH3 | Missense | M953I | 953/1137 | 228 | no |
| | | MSH6 | Missense | M1326T | 1326/1360 | 228 | no |
| | | POLE | Missense | P1164S | 1164/2286 | 140 | no |

Among the cancers without matched normal DNA, one showed a similarly high prevalence of rare protein-altering variants (>3,000) and a skewed distribution of rare protein-altering transversions. Thus, 9% of USC in this cohort have a hypermutator phenotype. Because of the skewing effect of the large number of mutations in these tumors, they were not included in subsequent analyses of mutation burden.

Example 3

Analysis of Single-Nucleotide Variants.

Among somatic mutations in the 30 remaining matched tumors, recurrences of somatic mutations at the same positions were identified. Accounting for the rate of protein-altering somatic mutations in these tumors ($1.1 \times 10^{-6}$) and the size of the exome, the likelihood of seeing the mutation twice by chance at any position among these tumors is $<10^{-3}$. Six genes with recurrent somatic mutations were identified (Table 1).

Figure 1B:
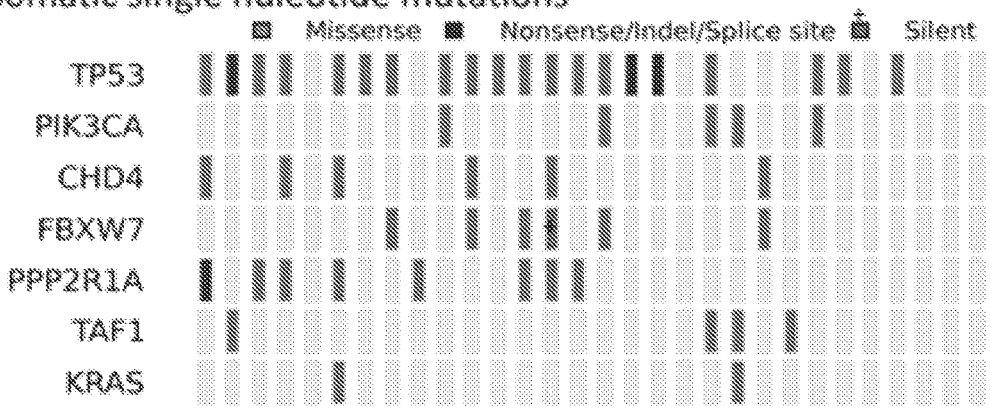
Figure 8:
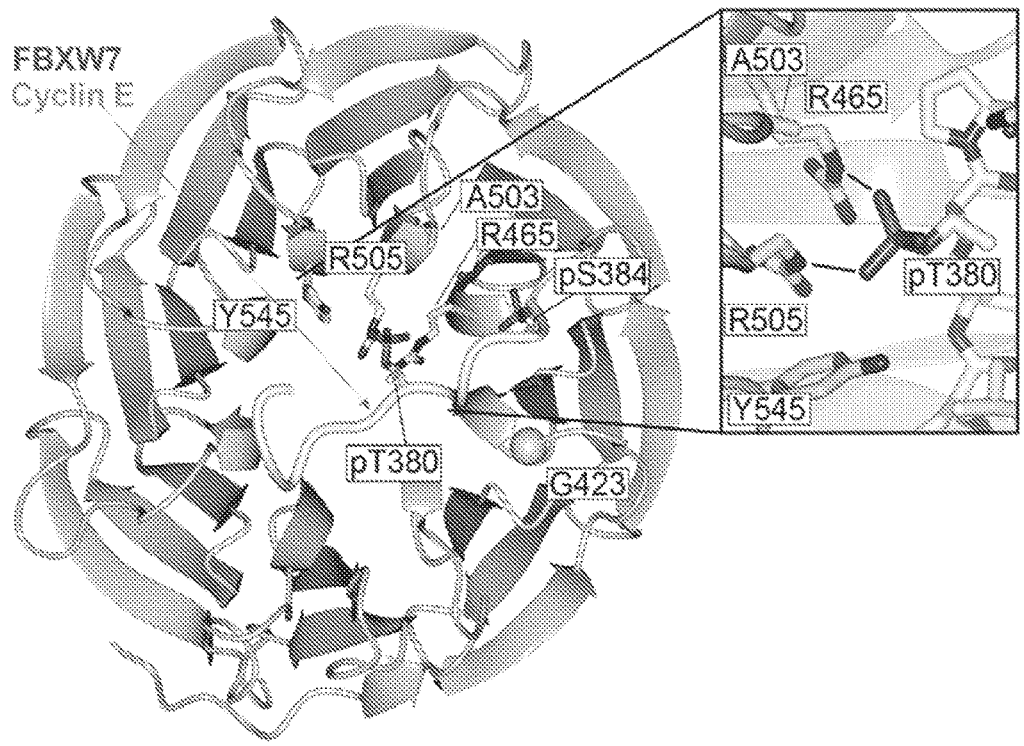
FIG. 8 is an illustration of the mapping of USC mutations onto the crystal structure of FBXW7 in complex with its high-affinity recognition motif in cyclin E. FBXW7 is shown in grey and the doubly-phosphorylated cyclin E in white, with phosphorylated residues labeled (PDB ID: 2OVQ). Residues of FBXW7 found mutated in USC are labeled. Inset shows close up of the interaction with black lines indicating hydrogen bonds.
Figures 9A, 9B:
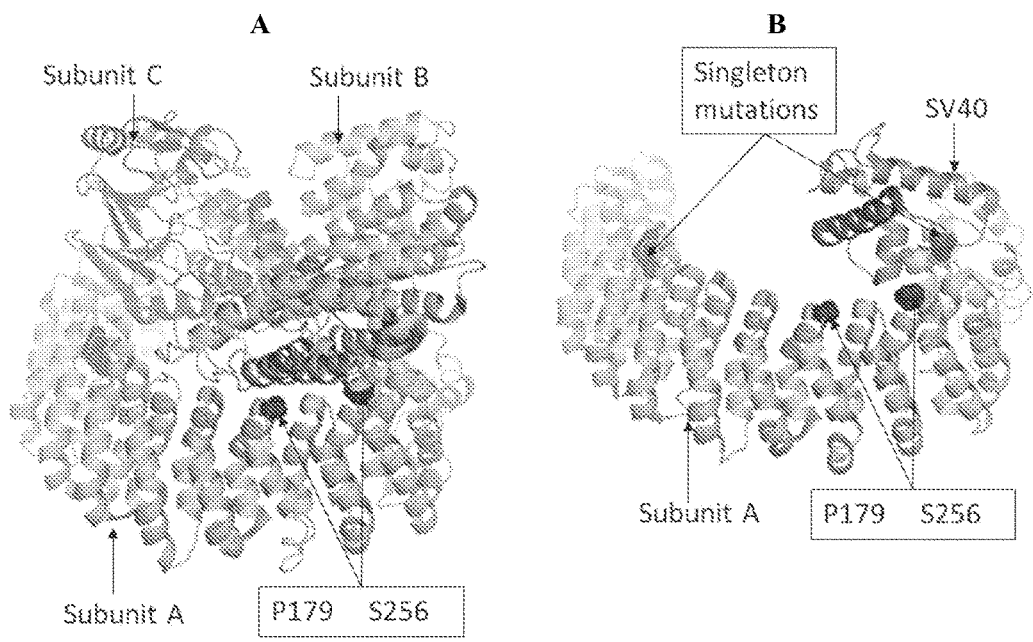
FIGS. 9A-9B is an illustration showing that somatic mutations in PPP2R1A may affect its interaction with other proteins.

These included well-established activating mutations in PIK3CA, the catalytic subunit of phosphoinositide-3 kinase (five tumors); the well-established G12V mutation in KRAS (three tumors) (Boguski and McCormick, Nature 366(6456): 643-654 (1993)); and a mutation at R465 in FBXW7 in four tumors. FBXW7 is the targeting component of a SCF-type 3 ubiquitin ligase, and R465 occurs in the WD40 domain involved in substrate recognition; mutation at this site prevents targeting of cyclin E for ubiquitination and degradation (FIG. 8) (Welcker and Clurman Nat Rev Cancer 8(2): 83-93 (2008); Hao et al., Mol Cell 26(1): 131-143 (2007)). Recurrent mutations also occurred at two sites in PPP2R1A, the constant regulatory subunit of serine-threonine phosphatase 2a. The P179R and S256F mutations occurred four and two times, respectively, and have been previously reported (Shih et al., Am J Pathol 178(4): 1442-1447 (2001)). These mutations occur at the interface where PPP2R1A interacts with regulatory B subunits that target the phosphatase to specific substrates; inhibition of this interaction by SV40 small t antigen plays a role in viral transformation (FIG. 9). Additional somatic mutations were found on the surface of PPP2R1A that interacts with the B or C (catalytic) subunit (Table 1). TP53, the well-characterized tumor suppressor gene, had five different positions mutated two or more times, and there were 19 additional single somatic mutations in this gene. Eighty-two percent of these mutations were in segments of somatic LOH (Table 1 and FIG. 1B). In addition to these previously described recurrent mutations, a recurrent mutation was found in CHD4/Mi2b (chromodomain-helicase-DNA-binding protein 4), an ATP-dependent chromatin-remodeling protein that is a major subunit of the Mi2b/nucleosome remodeling and deacetylase (NuRD) complex. Mutations in CHD4/Mi2b have not been previously associated with cancer. In addition, there were 10 other somatic or rare mutations in CHD4 among matched and unmatched tumors. Next, the overall increased somatic mutation burden in the 30 matched tumor-normal pairs was investigated. In this analysis, the probability of seeing >n mutations in each gene was determined, taking into account the overall rate of protein-altering somatic mutations in the matched tumor normal set ($1.1 \times 10^{-6}$) and the length of the protein-coding region in each gene. The level of expression of each gene from the expression data in normal human endometrium was also adjusted due to the higher somatic mutation rate found among genes with lower expression (Talbi et al., Endocrinology 147(3): 1097-1121 (2006)), which is consistent with the effects of transcription-coupled DNA repair reducing the mutation rate among expressed genes (Pleasance et al., Nature 463(7278): 191-196 (2010)). P values $<2.4 \times 10^{-6}$ were considered to represent a significant increase in mutation burden compared with that expected under the null hypothesis, accounting for the testing of 21,000 genes. This set was complemented with variants in the 22 unmatched tumors that occurred in genes that had at least one somatic mutation in the matched set and that had never been seen in >7,000 exomes in the Yale University and National Heart, Lung, and Blood Institute exome databases. Because no novel variants were found in any of these genes in the 30 germ-line samples of tumor-normal pairs, it can be infer that virtually all of these represent somatic mutations.

In the resulting set, the six genes with recurrent mutations were among the most frequently mutated genes. Included in this set was CHD4, which had six somatic mutations and five more novel variants found in the 22 unmatched tumors (Table 1 and FIG. 1B). Many of these 11 CHD4 mutations (FIG. 2), which all appear to be heterozygous, impair at least some normal CHD4 functions. CHD4 is a SWI2/SNF2 ATPase and part of the larger helicase superfamily 2 whose members share a similar catalytic core containing two RecA-like helicase domains. Conserved catalytic "signature" motifs have been well described and contain many residues required for catalysis of ATP hydrolysis and helicase activity (Lai et al., Nat Rev Cancer 11(8): 588-596 (2011)). Three CHD4 mutations (R957Q, RH27G, and R1162W) alter residues in these signature motifs (motif B, V, and VI, respectively) that are conserved from yeast to humans, and whose mutation has been shown to impair normal function. Similarly, there is a mutation in the second plant homeodomain (PHD) finger that normally binds methylated histone H3K9. This C464Y mutation disrupts one of the key cysteines that coordinate $Zn^{2+}$ binding. In addition, there are four mutations (Q1106R, I1109T, and two instances of F1112L) clustered in a short a-helix in ATPase lobe 2. Without wishing to be limited by theory, alteration of this helix might alter interaction with another protein in the complex.

Figures 2A, 2B, 2C, 2D:
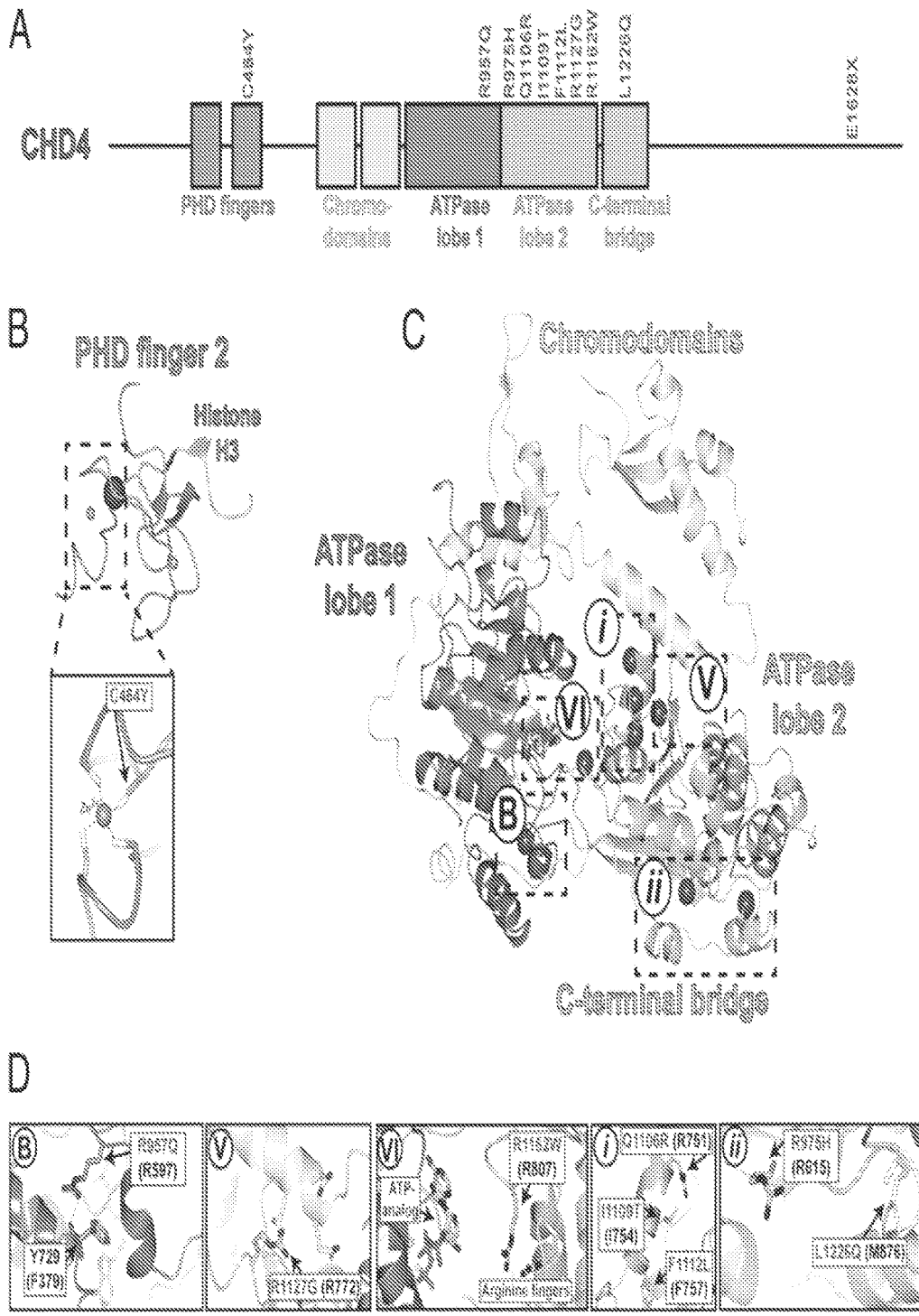
FIGS. 2A-2D are a series of figures that illustrate the mapping of USC mutations onto the crystal structure of CHD4.
Figures 3A, 3B:
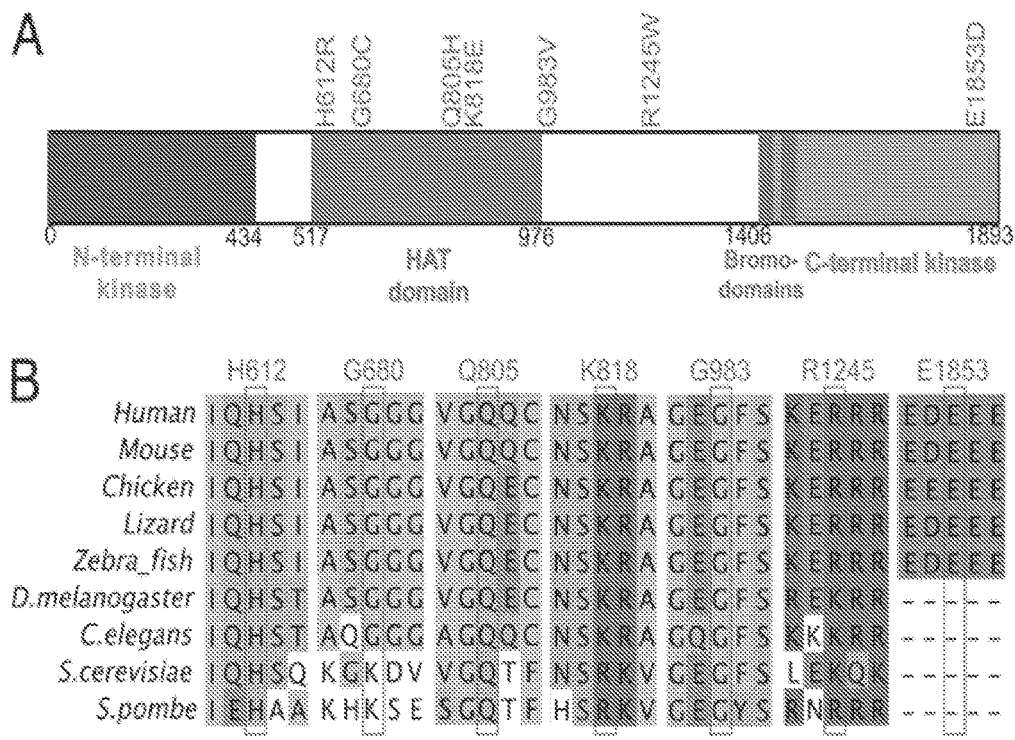
FIGS. 3A-3B are a series of graphs and figures that illustrate TAF1 functional domains and the mutation conservation analysis.

Additional mutations include two in a C-terminal bridge that links ATPase lobes 1 and 2 at positions that appear to stabilize this segment. Finally, there is a premature termination near the normal C terminus (FIG. 2). The high prevalence of CHD4 mutations, the clear implication of disrupted normal function by many CHD4 mutations, and the common genomic amplifications of the CHD4 gene (see CNV results in Example 4 below) implicate CHD4 mutations in USC. Another gene of interest was TAF1, an X-linked gene, which had four different somatic mutations and three additional variants in unmatched tumors (Table 1). TAF1 is the largest component and core scaffold of the TFIID basal transcription factor complex and has DNA-binding activity, histone acetyltransferase (HAT) activity, two kinase domains, and ubiquitin-activating/conjugating activity (Wassarman and Sauer, Cell Sci 114(Pt 16): 2895-2920 (2001)). It is known to be required for progression through the G1 phase of the cell cycle, promoting cyclin D expression (Hilton et al., Mol Cell Biol 25(10): 4321-4332 (2005)). Most of the seven TAF1 mutations lie in the HAT domain at positions that are extraordinarily well conserved; all are conserved in vertebrates and nearly all are conserved in yeasts (FIG. 3). Although the function(s) of these mutations in USC are uncertain, overexpression of TAF1 has been previously reported in human lung and breast carcinoma and found to be associated with poor tumor differentiation and high mitotic activity (Wada et al., Cancer Res 52(2):307-313 (1992)). Additional genes that meet thresholds for significantly increased burden in the entire set include PTEN, CDKN1A, and SPOP, as well as HCFC1R1, CTDSPL, Y1PF3, and FAM132A, genes not previously implicated in cancer. For each of these genes, mutations are predominantly at highly conserved positions, there are few if any silent mutations in the same gene, and quantitative PCR demonstrated expression of each of these genes in all available USC cell lines.

Example 4

Analysis of Copy Number Variations (CNVs).

Figure 1C:
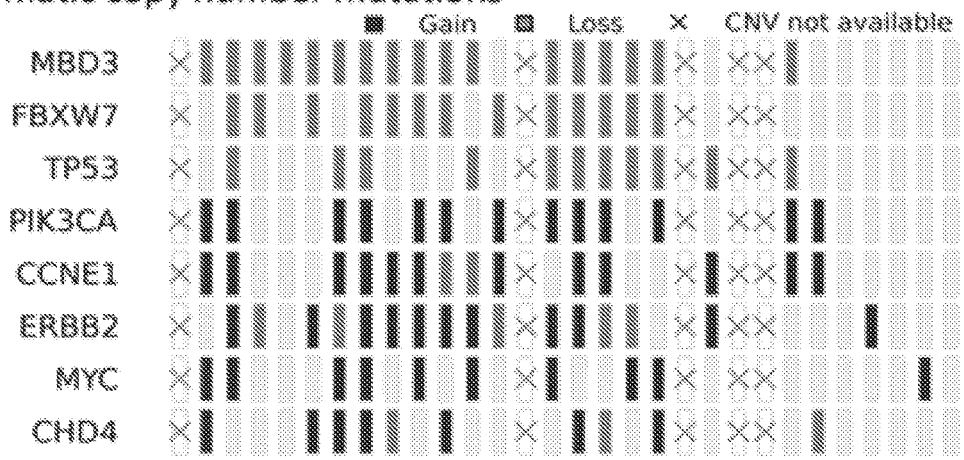
Figure 4:
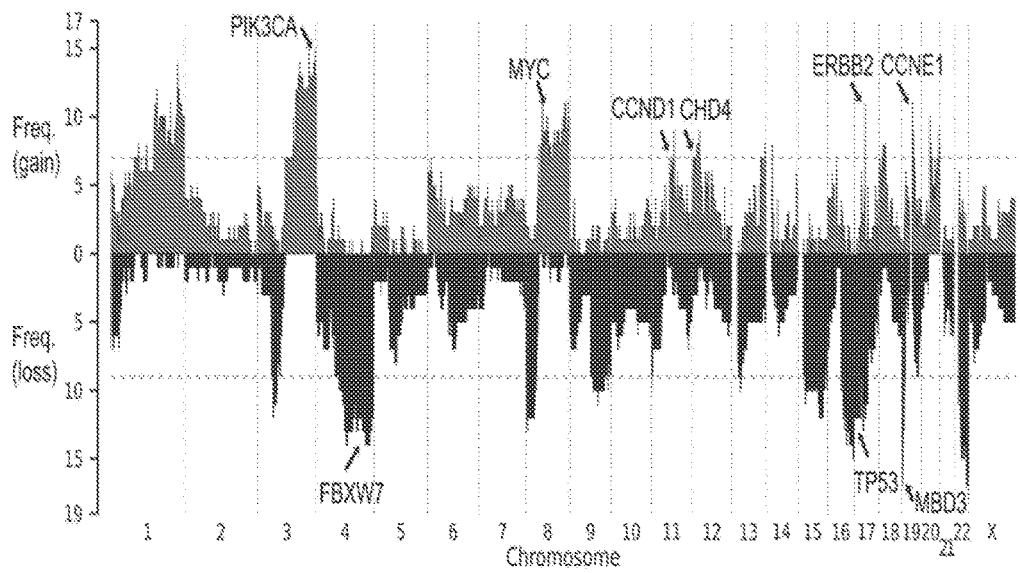
FIG. 4 is a series of graphs and figures that illustrates the copy-number profile of 25 USC tumors. Frequency of copy-number gain (grey) and copy-number loss (black) are plotted along the genome. Horizontal dotted line, genome-wide significance level for CNV gain (grey) and CNV loss (black). Genes of interest in significant CNV peak regions are labeled.
Figures 10A, 10B, 10C, 10D:
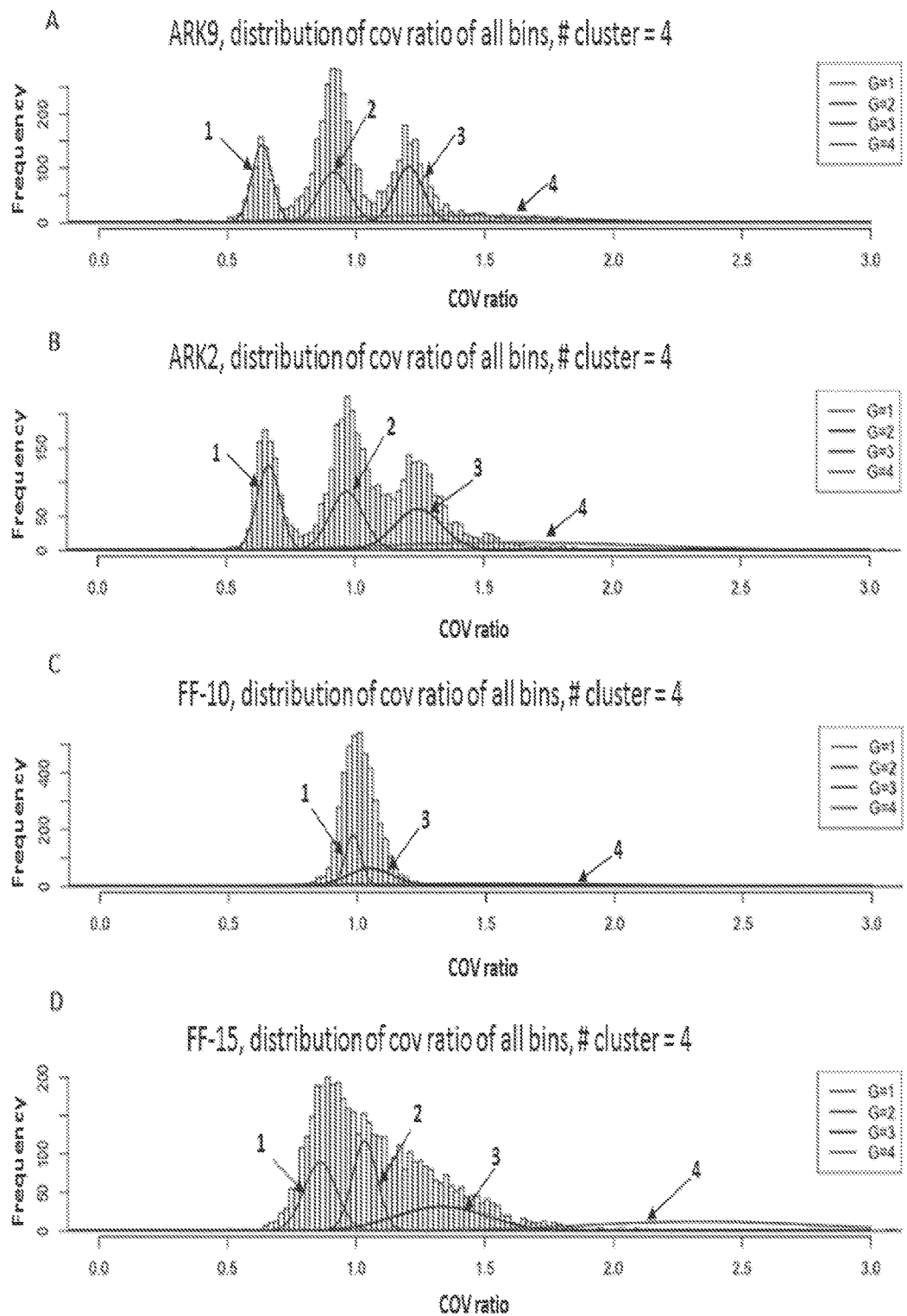
FIGS. 10A-10D are graphs that illustrate the patterns of distribution of coverage depth ratio in different USC samples. The distribution of coverage depth ratio (cov ratio) was plotted for each of the 34 matched normal tumor pairs. Unsupervised clustering was performed to identify potential clusters with coverage ratio deviated from 1 caused by copy number variation (curves 1, 2, 3 and 4). 4 examples representing typical distribution patterns in these samples are shown. Only samples with cov ratio patterns similar to FIGS. 10A-10C were used for further CNV analysis (n=25) while samples like FIG. 10D were discarded in CNV analysis due to noise.
Figure 11:
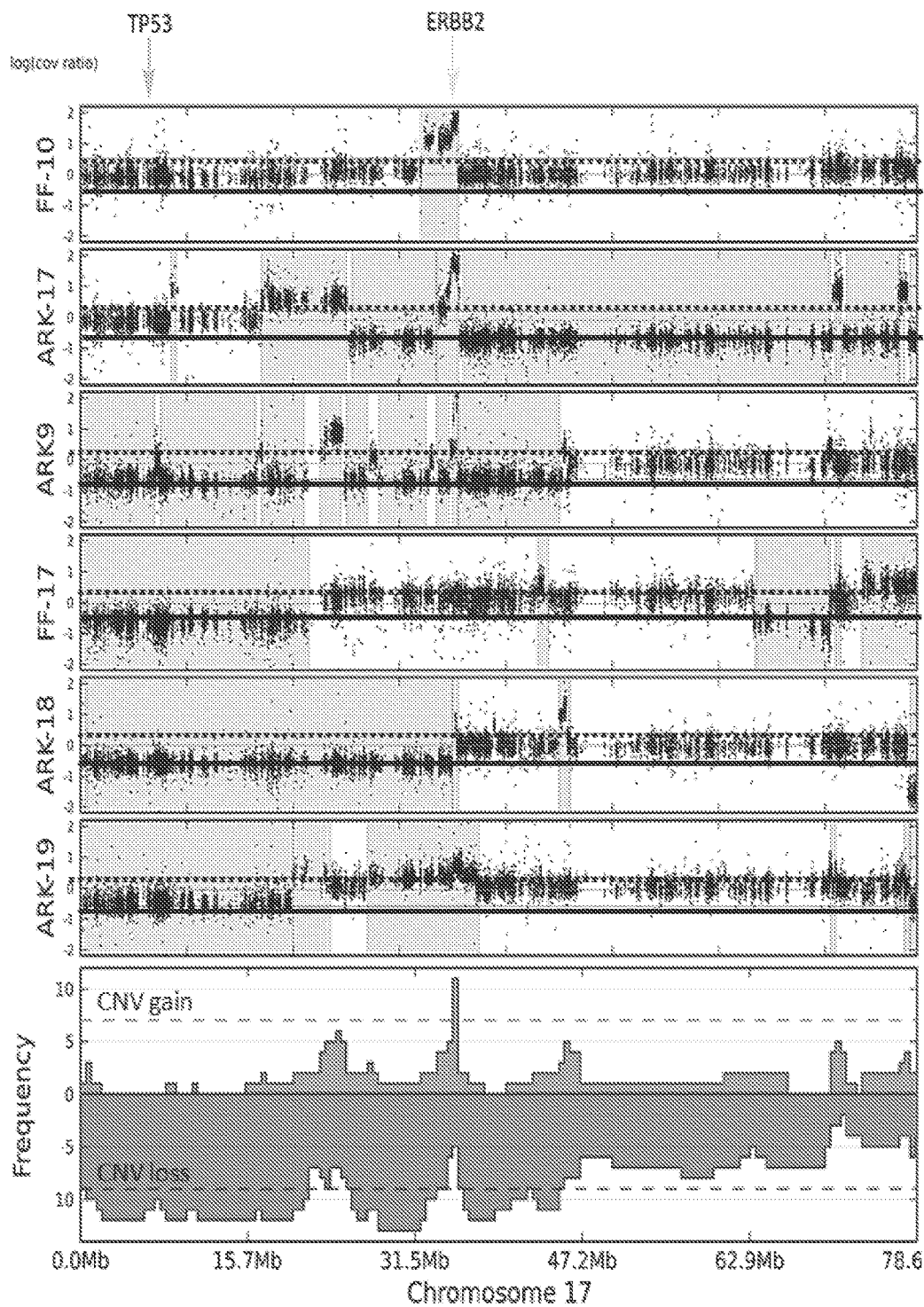
FIG. 11 is a graph that illustrates the focal amplification on chromosome 17 (ERBB2) and chr17p deletion (TP53). Log of coverage depth ratio is plotted across chromosome 17. 6 samples (FF-10, ARK-17, ARKS, FF-17, ARK-18 and ARK-19) are shown in parallel with the bottom subplot showing CNV frequency for all samples analyzed (n=25). The positions of ERBB2 and TP53 are marked. Horizontal dotted line, CNV duplication cluster center; horizontal black line, CNV deletion cluster center; horizontal grey line, copy neutral cluster center; horizontal dotted line in bottom frequency plot, CNV gain (Top line) and loss (Bottom line) genome wide significance level.
Figure 12:
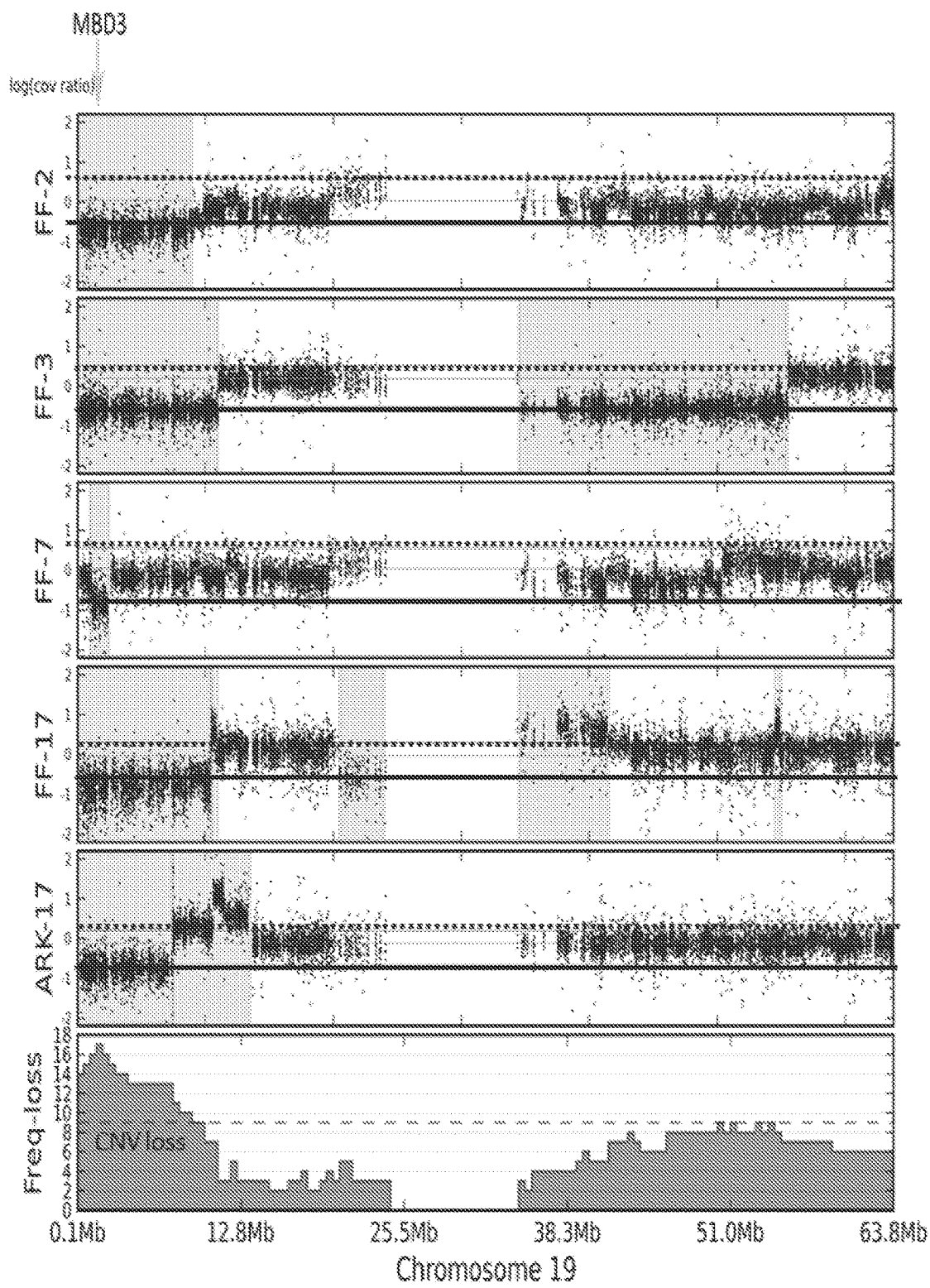
FIG. 12 is a graph that illustrates the focal deletion on chromosome 19p (MBD3). Log of coverage depth ratio is plotted across chromosome 19. 5 samples (FF-2, FF-3, FF-7, FF-17 and ARK-17) are shown in parallel with the bottom subplot showing CNV frequency for all samples analyzed (n=25). The position of MBD3 is marked. Horizontal dotted line, CNV duplication cluster center; horizontal black line, CNV deletion cluster center; horizontal grey line, copy neutral cluster center; horizontal dotted line in bottom frequency plot, CNV loss genome wide significance level.

Somatic CNVs were next assessed. For the 25 tumors in which read coverage distribution showed distinct modes (FIG. 10), comparing coverage depth of individual capture intervals from tumor and normal samples identified CNVs; CNVs were supported by significant deviation of the B allele frequency from the genome-wide average. The significance of CNVs affecting specific chromosome segments was assessed by Monte Carlo simulation, randomly distributing CNVs of the empirically observed sizes and numbers in each tumor in $10^8$ permutations to assess the distribution expected by chance alone. A significance threshold was established that provided a false discovery rate <0.25. Within each significant copy-number gain or loss, all CNVs that contained the most frequently altered segment were removed, and the remaining CNVs were reassessed to see if independent signals could be detected. 13 chromosome segments were identified with more frequent gains of copy number and 12 with more frequent deletions than expected by chance (FIG. 4). Among these, focal amplification of the segment of chromosome 17 that contains ERBB2 in 11 of the 25 tumors (44%) (FIG. 11), large duplications that include the PIK3CA locus in 60%, and a small duplication of chromosome 19 containing CCNE1 in 48% (Table 5 below) were found. There was also amplification of a large segment of chromosome 8 containing MYC in 11 (44%) tumors and amplification of a segment of chromosome 12 that included CHD4 in 7 (28%) tumors (FIG. 1C). Among deletions, TP53 was deleted in 44% of tumors. The most frequent somatic deletions were small (0.5 Mb) deletions on chromosomes 19 and 22, which occurred in 68% and 72% of tumors, respectively (FIG. 12 and Table 6 below). Most interestingly, the chromosome 19 interval contains MBD3, which is a component of the same SWI/SNF complex as CHD4 (Flaus A, et al., (2006). Nucleic Acids Res 34(10): 2887-2905). The chromosome 22 interval includes a number of interesting genes, including three in the MAP kinase pathway, HDAC10, and PPP6R2.

TABLE 5

Significantly duplicated intervals.

| Chr | Start | End | Size | Frequency | Gene number: gene list* | Cancer gene** |
|---|---|---|---|---|---|---|
| chr3 | 173500000 | 195000000 | 21500000 | 15 | 128 | ETV5, PIK3CA, LPP, SOX2, BCL6, EIF442 |
| chr1 | 223500000 | 224500000 | 1000000 | 14 | 15: DNAH14, EPHX1, LBR, H3F3A, LIN9, H3F3AP4, ENAH, LEFTY2, SRP9, LEFTY1, ACBD3, TMEM63A, C1orf55, PYCR2, MIXL1 | H3F3A |
| chr17 | 35000000 | 35500000 | 500000 | 11 | 21: NEUROD2, TCAP, PGAP3, PPP1R1B, ORMDL3, ERBB2, GSDMA, GSDMB, PSMD3, MIR4728, CSF3, MED24, PNMT, GRB7, THRA, STARD3, SNORD124, LRRC3C, MIEN1, IKZF3, ZPBP2 | ERBB2 |
| chr19 | 34500000 | 35500000 | 1000000 | 11 | 7: PLEKHF1, VSTM28, CCNE1, POP4, LOC284395, C19orf12, URI1 | CCNE1 |
| chr8 | 55000000 | 142000000 | 87000000 | 11 | 373 | NCOA2, CHCHD7, EXT1, TCEA1, NDRG1, MYC, PLAG1, COX6C, HEY1 |
| chr20 | 29500000 | 30000000 | 500000 | 10 | 16: BCL2L1, TPX2, PDRG1, REM1, MYLK2, FOXS1, ID1, COX4I2, TTLL9, PSIMCT-1, DUSP15, DEFB124, DEFB123, HM13, MIR3193, LINC00028 | |

TABLE 5-continued

Significantly duplicated intervals.

| Chr | Start | End | Size | Frequency | Gene number: gene list* | Cancer gene** |
|---|---|---|---|---|---|---|
| chr11 | 75500000 | 76000000 | 500000 | 9 | 4: UVRAG, PRKRIR, WNT11, C11orf30 | |
| chr12 | 23500000 | 24000000 | 500000 | 9 | 1: SOX5 | |
| chr14 | 21500000 | 22000000 | 500000 | 9 | 0 | |
| chr13 | 111000000 | 113000000 | 2000000 | 8 | 13: MCF2L-AS1, PROZ, C13orf35, F7, PCID2, MCF2L, TUBGCP3, CUL4A, SPACA7, LAMP1, ATP11A, F10, SOX2 | |
| chr18 | 12500000 | 23000000 | 10500000 | 8 | 57 | SS18, ZNF521 |
| chr16 | 29500000 | 30000000 | 500000 | 7 | 24: DOC2A, ASPHD1, LOC440356, PRRT2, CDIPT, QPRT, SLC7A5P1, PPP4C, SPN, MVP, FAM578, ZG16, ALDOA, INO80E, SEZ6L2, TAOK2, KCTD13, MAZ, KIF22, C16orf92, C16orf53, TMEM219, C16orf54, HIRIP3 | |
| chr6 | 11000000 | 11500000 | 500000 | 7 | 6: SYCP2L, ERVFRD-1, NEDD9, C6orf228, ELOVL2, LOC100506409 | |

TABLE 6

Significantly deleted intervals.

| Chr | Start | End | Size | Frequency | Gene number: gene list* | Cancer gene** |
|---|---|---|---|---|---|---|
| chr22 | 49000000 | 49500000 | 500000 | 18 | 24: LMF2, CHK6-CPT15, ODF38, SBF1, MIOX, MAPK11, MAPK12, CHKB, PLXNB2, SYCE3, FAM116B, ADM2, CPT18, PPP6R2, KLHDC7B, SHANK3, MAPKBIP2, NCAPH2, ARSA, TYMP, LOC100144603, HDAC10, TUBGCP6, SCO2 | |
| chr19 | 1500000 | 2000000 | 500000 | 17 | 17: REXO1, SCAMP4, KLF16, TCF3, ONECUT3, UQCR11, MIR1909, ADAT3, ATP8B3, MKNK2, CSNK1G2-AS1, LOC100288123, MBD3, CSNK1G2, MEX3D, FAM108A1, BTBD2 | TCF3 |
| chr16 | 85500000 | 88000000 | 2500000 | 15 | 35: TRAPPC2L, LOC100287036, CDH15, ZCCHC14, ZFPM1, JPH3, KLHDC4, ANKRD11, MGC23284, PABPN1L, CDT1, CBFA2T3, CTU2, C15orf95, LOC400558, ZC3H18, MAP1LC38, LINC00304, CA5A, SLC7A5, MIR4722, BANP, IL17C, PIEZO1, ACSF3, GALNS, APRT, CYBA, MVD, SNAI3, RNF166, SLC22A31, ZNF469, FBXO31, ZNF778 | CBFA2T3 |
| chr4 | 99000000 | 179000000 | 80000000 | 14 | 310 | FBXW7, TET2, IL2, RAP1GDS1 |
| chr17 | 28000000 | 32000000 | 4000000 | 13 | 63 | TAF15 |
| chr8 | 2000000 | 3500000 | 1500000 | 13 | 2: MYOM1, CSMD1 | |
| chr15 | 73000000 | 85000000 | 12000000 | 12 | 135 | |
| chr3 | 53000000 | 55500000 | 2500000 | 12 | 15: CACNA2D3, SELK, ESRG, ACTR8, CACNA1D, PRKCD, SFMBT1, TKT, LRTM1, DCP1A, CHDH, RFT1, WNT5A, MIR1303, IL17RB | |
| chr9 | 94500000 | 96000000 | 1500000 | 11 | 19: MIRLET7F1, MIRLET7D, FGD3, ANKRD19P, NINI1, FAM120A, ZNF484, PTPDC1, LOC158257, WNK2, BARX1, C9orf89, C9orf129, MIR4291, MIRLET7A1, FAM120AOS, PHF2, BICD2, SUSD3 | |

TABLE 6-continued

Significantly deleted intervals.

| Chr | Start | End | Size | Frequency | Gene number: gene list* | Cancer gene** |
|---|---|---|---|---|---|---|
| chr11 | 0 | 500000 | 500000 | 10 | 19: LOC100153161, ODF3, RIC8A, NLRP6, ANO9, IFITM5, IFITM2, PTDSS2, IFITM1, PSMD13, SCGB1C1, BAGALNTA, PKP3, ATHL1, SIGIRR, IFITM3, BET1L, SIRT3, RNH1 | |
| chr13 | 28500000 | 31000000 | 2500000 | 10 | 15: C13orf33, TEX26, USPL1, UBL3, LOC440131, LOC728437, LINC00426, KATNAL1, SLC7A1, TEX26-AS1, MTUS2, ALOX5AP, B3GALT1, HMGB1, HSPH1 | |
| chr19 | 50000000 | 54500000 | 4500000 | 9 | 186 | ERCC2 |

Example 5

The exome sequencing of a USC cohort, which is five times larger than those recently described, defines the genetic hallmarks of uterine serous cancer. Significantly increased mutation burden were found in 14 genes, including the previously identified and well-recognized cancer genes TP53, PIKC3A, PPP2R1A, KRAS, and PTEN, FBXW7, and CDKN1A.

The high frequency of single-nucleotide variants (SNVs) in CHD4, which was mutated in 19% of tumors and was the third most frequently mutated gene, was noteworthy. These mutations were diverse and predominantly at highly conserved positions from yeast to humans, and several have been previously shown to cause loss of function. Nonetheless, because CHD4 has many functional domains, it is possible that not all CHD4 functions are lost. Indeed, there appears to be clustering of mutations in particular domains, and there are seven copy-number gains that include CHD4.

Similarly, mutations in TAF1, a component of the core RNA polymerase II machinery, are found in 13% of tumors, with mutations at positions conserved throughout yeasts. Because TAF1 has diverse biochemical functions, the observed clustering of mutations in the HAT domain does not require that these mutations are null for all TAF1 functions. One known function of TAF1 is promotion of cyclin D expression; overexpression of cyclin D is itself known to promote cell cycle progression and proliferation and is frequently amplified in cancers. Notably, seven tumors had amplification of the segment of chromosome 11 containing CCND1 (FIG. 4).

Several other genes show marginal statistical significance; these include known cancer genes such as PTEN and CDKN1A as well as SPOP, which target proteins for ubiquitination via its MATH domain. SPOP has recently been shown to have clustered mutations in its MATH domain in prostate cancer; the two USC mutations are at different sites in the MATH domain. Additional genes not previously implicated in cancer include HCFC1R1, CTDSPL, YIPF3, and FAM132A.

The herein results demonstrate that somatic CNVs play a major role in the pathogenesis of USC, one that is likely at least as important as somatic point mutations. Interestingly, the most frequent CNV was a small deletion found in 68% of tumors affecting a short segment of chromosome 19 that contains only 17 genes. Among these genes is MBD3, which is part of the same chromatin-remodeling complex—NuRD—as CHD4. Additionally, there were seven copy-number gains of the segment of chromosome 12 that includes CHD4, all of which were in samples with MBD3 deletions. This complex deacetylates histones, repressing gene expression. Collectively, these findings add to the growing list of genes involved in chromatin remodeling that are mutated in cancer (Turcan et al., Nature 483 (7390): 479-483 (2012); Wang et al., Nat Genet 43 (12): 1219-1223 (2011)).

CNV analysis of USC also identified frequent amplifications, including the well-known cancer genes PIK3CA (60%) and ERBB2 (encoding HER2/neu; 44%). ErbB2 overexpression has been previously reported to be associated with cancer cell proliferation, poor survival, and resistance to therapy in multiple human tumors including USC. Moreover, ErbB2 functions as an upstream regulator of the PIK3CA/AKT/mTOR-signaling pathway. These findings suggest common involvement of this pathway in USC and the possible utility of Food and Drug Administration-approved antibodies (i.e., trastuzumab, pertuzumab) or small molecule TK inhibitors used either alone or in combination with anti-mTOR, AKT, and/or PIK3CA active agents.

Another frequent somatic amplification (found in 44% of tumors) included a small segment of chromosome 19 that harbors CCNE1. CCNE1 encodes cyclin E1 and is known to regulate the transition from the G1 phase to the S phase. High levels of CCNE1 accelerate the transition through the G1 phase, and its accumulation is common in a number of cancers. Most interestingly, CCNE1 degradation is mediated by binding to FBXW7 followed by ubiquitination via the SCF complex. Seventeen percent of USC harbor recurrent mutations in FBXW7 that abrogate CCNE1 binding (FIG. 8). These observations suggest that inhibition of CCNE1 activity may have efficacy in patients harboring mutation in this pathway.

Figure 5:
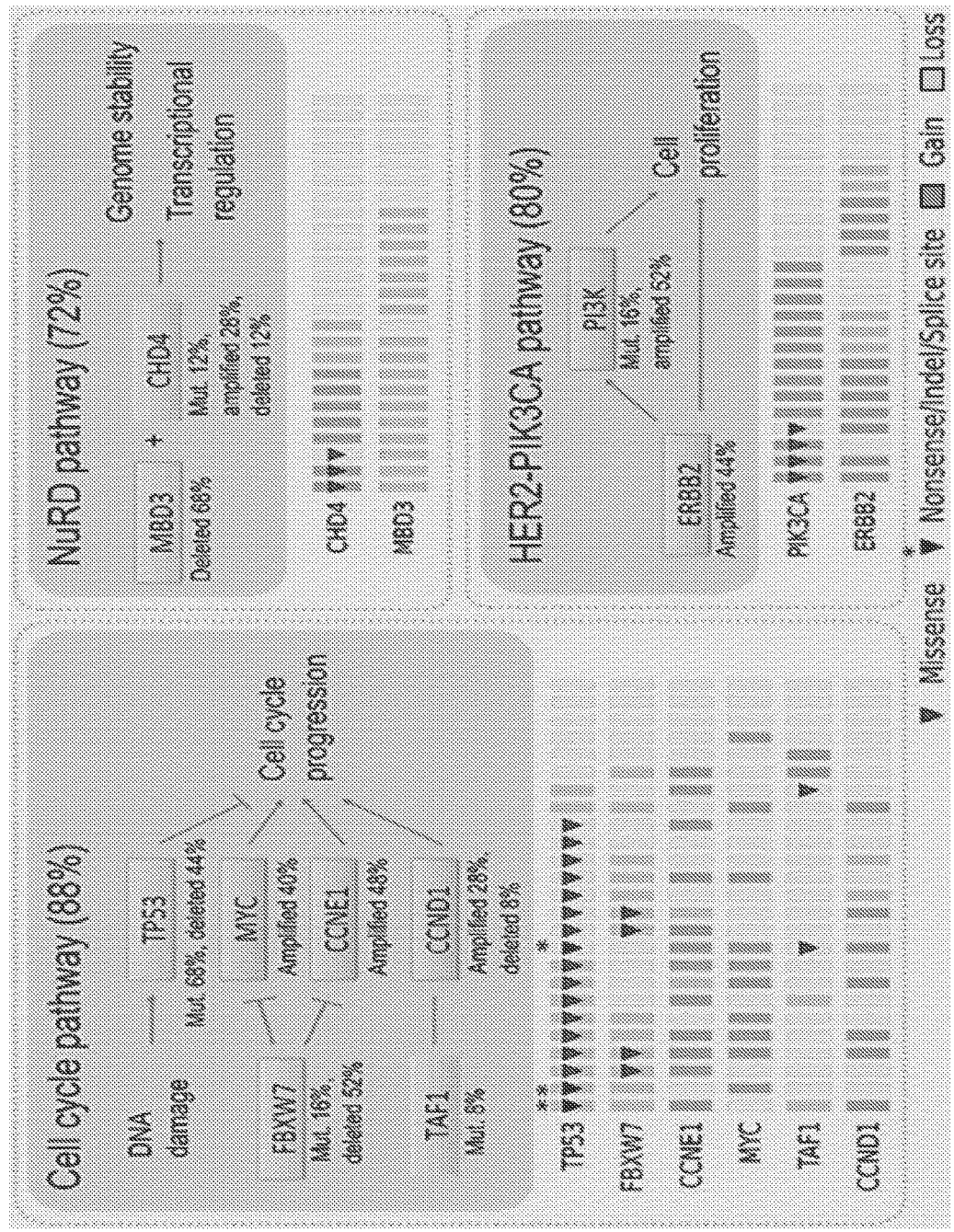
FIG. 5 is a graph that illustrates the major altered pathways in USC. The altered percentages shown for genes and pathways come from the 25 matched tumors with CNV information. Genes are marked based on their activity in the pathway diagram. Predicted activated: MYC, CCNE1 and CCND1; Predicted inactivated: TP53 and FBXW7; Uncertain at this stage: TAF1; lines with blunt end, inhibiting effect; lines with pointed end, promoting effect; dotted line, uncertain. Mutation and CNV status for each gene across the 25 samples are shown at the bottom following the pathway diagram.
Figure 13:
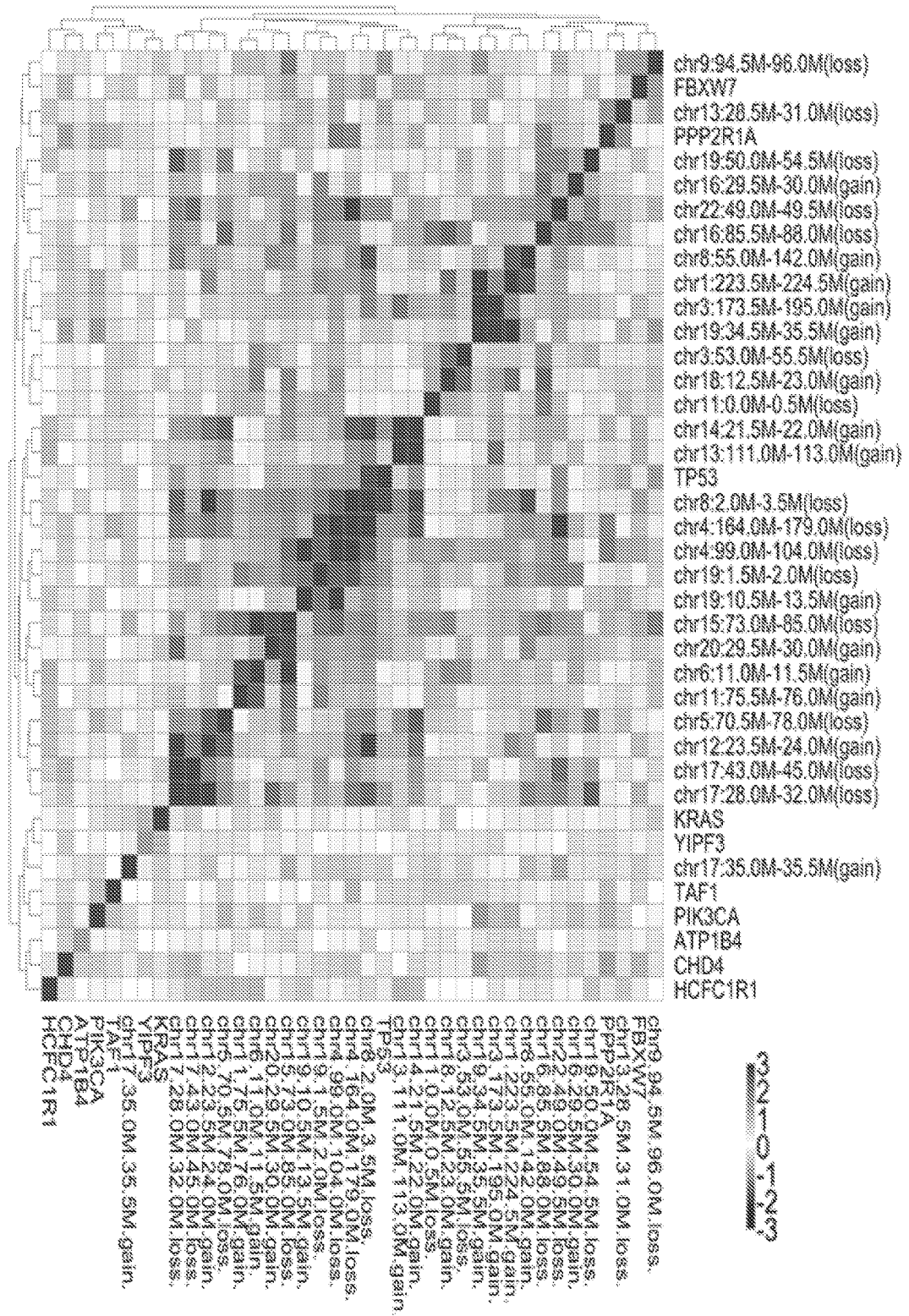
FIG. 13 is a heat map graph that illustrates the pairwise correlation/exclusion study for significantly mutated genes and significant CNVs. Heat map depicting patterns of correlation and exclusion in USC is shown. Overall a high level of correlation is depicted. Significantly mutated genes from 30 matched samples and significant CNV events from 25 matched samples were included in this study. Pairwise correlation or exclusion p value was calculated based on permutation. Correlation (1, 2, 3); Exclusion (−1, −2, −3).

Collectively, the results implicate frequent mutations in several pathways in USC, including specific genes in DNA damage, chromatin remodeling, cell cycle, and cell proliferation pathways (FIG. 5). Analysis of correlation and anti-correlation of all possible pairs of significant mutations did not provide evidence of strong associations (FIG. 13). Nonetheless, a large fraction of tumors shared mutations affecting genes in different pathways such as TP53, PIK3CA, MBD3, and FBXW7. Additionally, 9% of USC were found to carry a very high number of somatic mutations with many somatic mutations in mismatch repair and POLE genes. This distribution is distinct from the remainder (median 36 protein-altering mutations, all <100). These USC tumors are notable for being relatively frequent and for having a uniformly very high number of mutations, more than those seen in 90% of colon cancers with the mutator phenotype. Despite the remarkable somatic mutation burden, these tumors had no identified CNVs.

Figure 14:
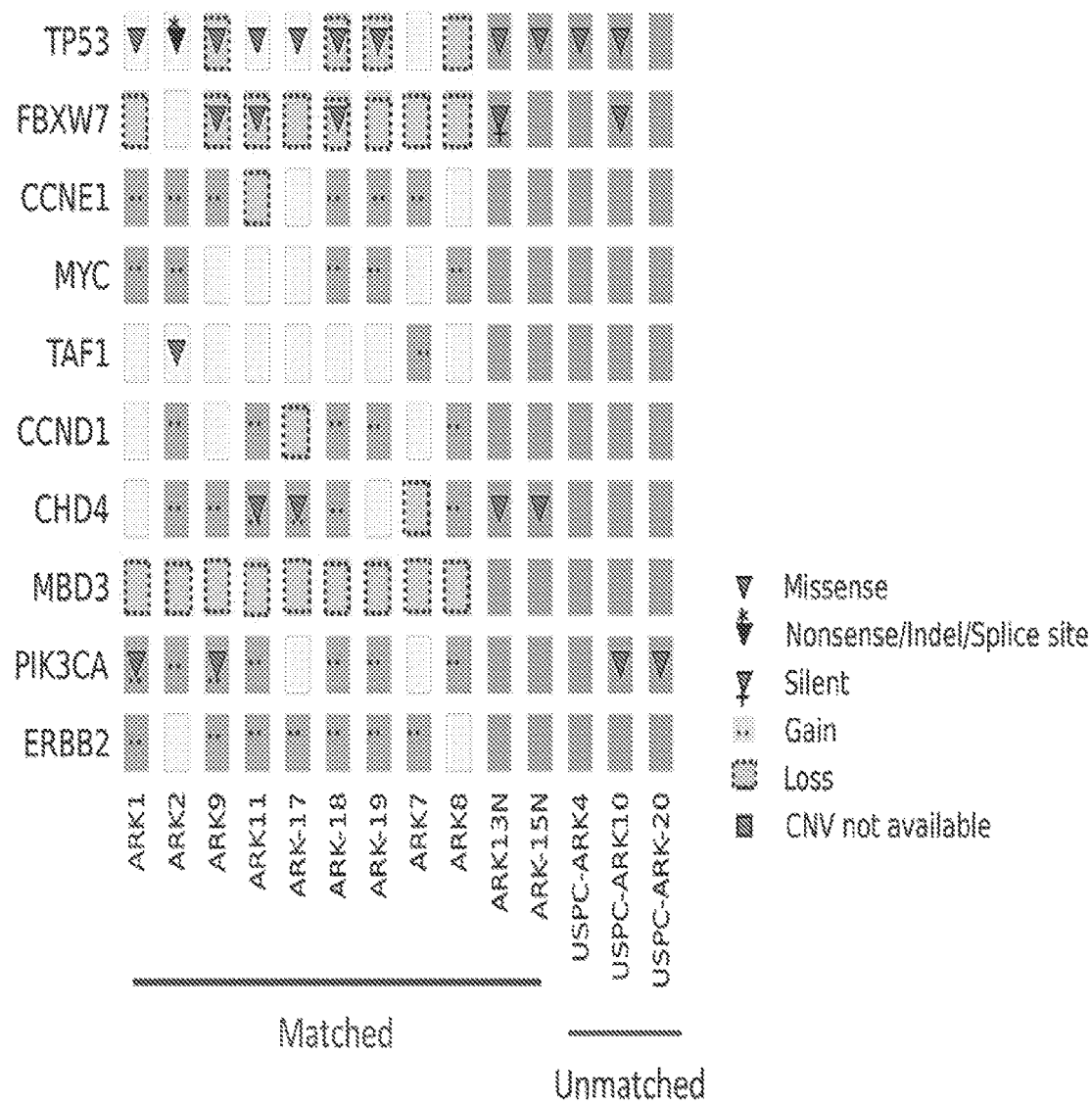
FIG. 14 is a graph that illustrates the mutation profile in 14 USC cell lines. The distribution of SNVs and CNVs in 14 USC cell lines is shown. CNV calls were not made in cell lines without matched normal DNA for comparison. One additional cell line had the hypermutator phenotype.

The establishment of 15 USC cell lines with different mutation profiles (FIG. 14) provides the opportunity for in vitro assessment of whether a mutation profile is predictive of drug response. For example, the finding that MMR-defective colorectal cancers may respond favorably to poly (ADP ribose) polymerase inhibitors raises the question of whether the same may apply to USC with the hypermutator phenotype.

USC and high-grade serous ovarian carcinoma (HG-SOC) are histologically similar gynecological tumors characterized by a highly aggressive biologic behavior. Exome sequencing of HG-SOC has been recently reported by The Cancer Genome Atlas Research Network (Cancer Genome Atlas Research Network, Nature 474 (7353): 609-615 (2011)). TP53 was mutated in 95% of these cancers, with no other gene with somatic SNVs in more than 6% and only four (BRCA1, BRCA2, CSMID3, and FAT3) that were mutated in more than 3%. USC shows a lower frequency of TP53 mutation (59%), 5 genes mutated in 13-23% of tumors, 10 more genes mutated in 3-10%, and no BRCA1 or BRCA2 mutations (Table 7 below). These findings indicate substantial differences in the genetics of USC and HG-SOC.

The results described herein define the genetic landscape of USC and identify specific pathways that are frequently mutated in these tumors. These findings will guide further research and targeted therapies against this highly aggressive variant of endometrial cancer.

TABLE 7

Comparison with high-grade ovarian serous carcinoma (HGS-OvCa)

| | USC(n = 52) | | HGS-OvCa(n = 316) | |
|---|---|---|---|---|
| | Affected sample number | Percentage | Affected sample number | Percentage |
| PIK3CA* | 12 | 23.08% | 5 | 1.58% |
| CHD4* | 10 | 19.23% | 8 | 2.53% |
| FBXW7* | 9 | 17.31% | 3 | 0.95% |
| PPP2R1A* | 8 | 15.38% | 4 | 1.27% |
| TAF1* | 7 | 13.46% | 5 | 1.58% |
| KRAS* | 3 | 5.77% | 2 | 0.63% |
| PTEN* | 3 | 5.77% | 0 | 0.00% |
| HCFC1R1* | 2 | 3.85% | 0 | 0.00% |
| CDKN1A* | 2 | 3.85% | 1 | 0.32% |
| CTDSPL* | 2 | 3.85% | 0 | 0.00% |
| YIPF3* | 2 | 3.85% | 0 | 0.00% |
| SPOP* | 2 | 3.85% | 1 | 0.32% |
| FAM132A* | 2 | 3.85% | 0 | 0.00% |
| TP53** | 31 | 59.62% | 303 | 95.89% |
| BRAC1* | 0 | 0.00% | 11 | 3.48% |
| CSMD3* | 0 | 0.00% | 19 | 6.01% |
| NF1* | 1 | 3.33% | 13 | 4.11% |
| CDK12* | 0 | 0.00% | 9 | 2.85% |
| FAT3* | 1 | 6.67% | 19 | 6.01% |
| GABRA6* | 0 | 0.00% | 7 | 1.90% |
| BRCA2* | 0 | 0.00% | 10 | 3.16% |
| RB1* | 0 | 0.00% | 6 | 1.90% |

Example 6

Figure 15:
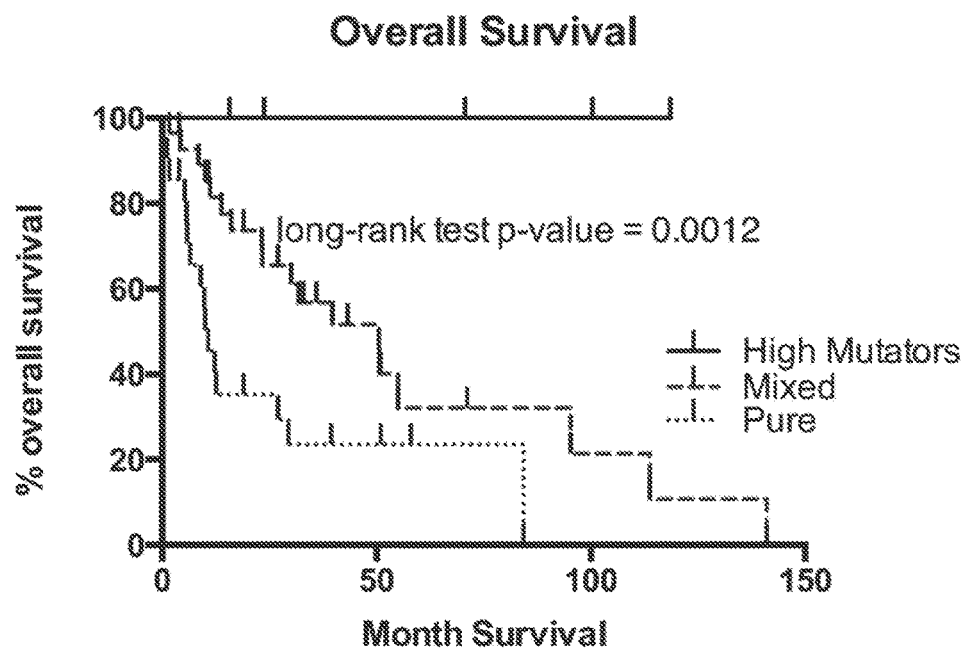
FIG. 15 is a graph that illustrates the survival analysis of USC patients. The Kaplan-Meyers survival curves is shown for the 57 USC patients (5 harboring a hypermutator phenotype vs 52 moderately mutated reported in the genetic landscape analysis, Zhao et al., Proc Natl Acad Sci USA 110(8):2916-2921 (2013)) according to mixed and pure tumor histology. P value was calculated by the log-ranked test for survival differences.

Patients diagnosed with hypermutator USC phenotype (i.e. POLE gene mutated) experience an extraordinary better prognosis when compared to the remaining USC patients (FIG. 15). These results were surprising considering that 2 of 5 of the long term USC survivors in the series harbored advanced stage disease (i.e., stage III) and the remaining 3 harbored a stage I-B of the disease (risk of recurrence up to 80%) (Fader et al., Gynecologic Oncology. 129(1):244-50, (2013)). Importantly, the impressive survival results reported herein in patients harboring hypermutator Type II USC have recently been confirmed by the similarly excellent survival results found in 7% (17 out of 248) of the Type I endometrial cancer patients harboring proofreading POLE mutations reported by the cancer genome atlas (TCGA) group (The Cancer Genome Atlas Research Network. Nature. 497:67-73, (2013)).

Example 7

Figure 16:
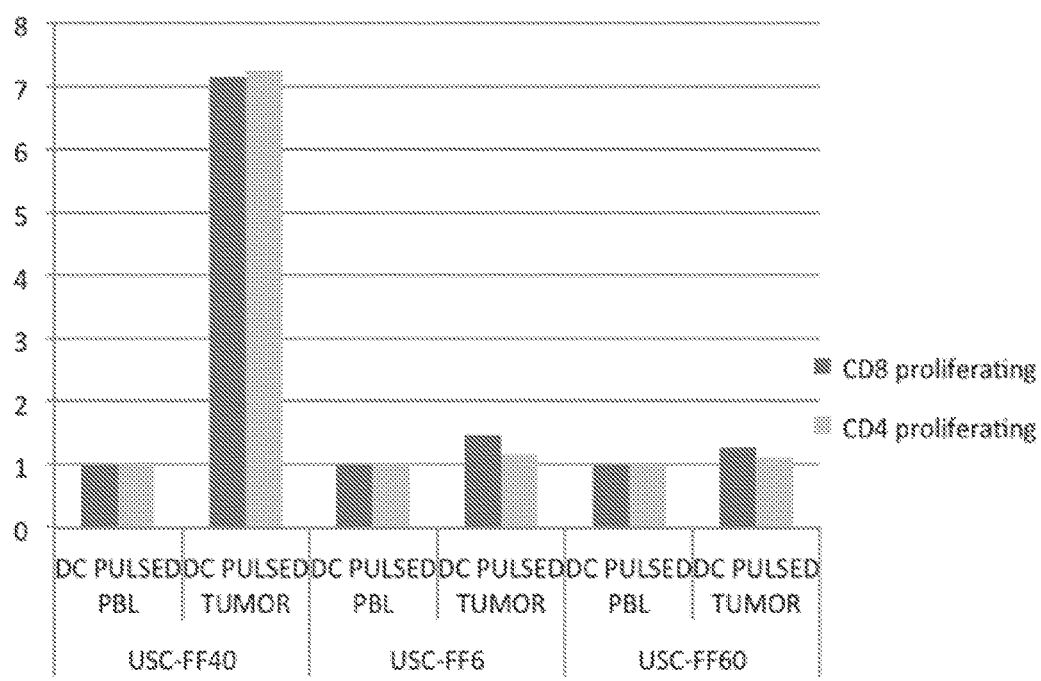
FIG. 16 is a histogram that illustrates the proliferation in CD4 and CD8+ T cells from USC (i.e., Type II) and endometrial endometrioid (Type I) patients in vitro. High proliferation in CD4+ and CD8+ T cells stimulated with USC-lysate-pulsed autologous dendritic cells (DC) versus control peripheral blood lymphocytes-(PBL)-lysate-pulsed autologous DC were detected only in patients harboring POLE ultramutated tumors. USC-FF40 (POLE-mutated USC patient harboring an ultramutated phenotype). USC-FF6 and USC-FF60 (control USC patients with tumors harboring wild type POLE).

As representatively demonstrated in FIG. 16 for 3 USC patients, only patients harboring an ultramutated tumor (i.e., POLE mutated, USC-FF40) develop strong proliferative responses in autologous CD4+ and CD8+ T cells when stimulated with autologous-monocyte derived dendritic cells loaded with USC lysate. Proliferation in CD4+ and CD8+ T cells from POLE mutated patients was significantly higher (p=0.01) when compare to that induced in control patients harboring USC with wild type POLE (i.e., USC-FF6 and USC-FF60). This data provides novel information for the identification of a subset of biologically aggressive USC with unique prognostic features and biological properties. POLE ultramutated tumors induce strong proliferative responses in autologous CD4+ and CD8+ T cells stimulated with USC-lysate-pulsed autologous DC.

The results presented herein demonstrate the high immunogenicity of these ultramutated tumors and suggest that immunotherapeutic strategies may potentially be highly beneficial in human cancer patients harboring tumors with a POLE high mutator phenotype.

Example 8

Figure 17:
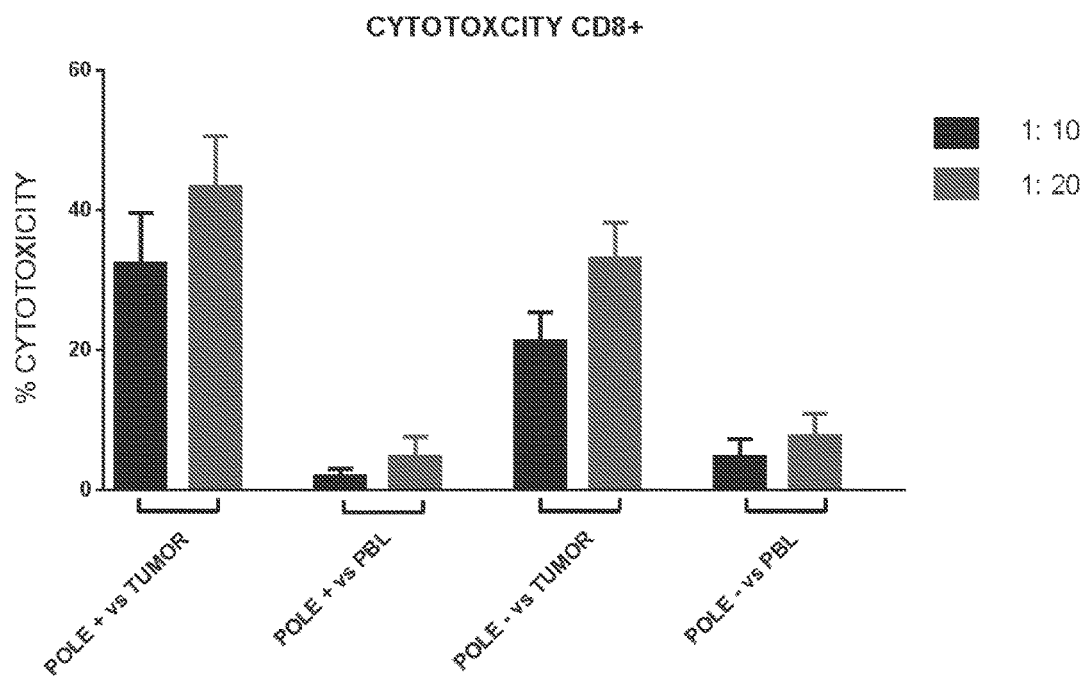
FIG. 17. is a histogram that illustrates tumor specific CD8+ CTL responses induced by tumor lysate-pulsed DCs in POLE mutated vs POLE wild type endometrial cancer patients in vitro, measured in 4 h $^{51}$Cr-release assays. Percentage lysis (±standard deviation) at a 10:1 and 20:1 effector/target cell ratio are shown against autologous tumor cells and autologous PHA-stimulated normal lymphocytes or LCL for the two groups of endometrial cancer patients. Although in most of the experiments CD8+ T cells from POLE mutated patients were found more cytotoxic against autologous tumor cells when compared to CTLs from POLE wild type endometrial cancer patients, this difference was not significant (P=0.305).

Tumor-Specific CD8+ Cytotoxic T Cell Responses Against POLE Mutated Vs POLE Wild Type Cancers Cytotoxicity assays were conducted after a minimum of 4 weeks after initiation of T lymphocyte cultures as described in the methods. The results presented in FIG. 1 represent the mean of 2 to 5 separate cytotoxicity assays for each patient. CD8+ T cell cytotoxicity against autologous tumor-cell targets was demonstrated in all patients where viable autologous tumor target cells were available (i.e., three harboring POLE mutated tumors vs three harboring POLE wild type tumors, Table 8 below). Autologous tumor cell killing ranged from 26.2 to 67.6% in POLE mutated patients vs. 18.3 to 40.2% in POLE wild type at 20 effectors per target. Cytotoxicity against autologous PHA-stimulated or autologous EBV-transformed LCL was detectable at low to negligible levels in all patients (FIG. 17). The absence of significant cytotoxicity showed that, although these cells were highly cytotoxic against autologous tumor cells, they failed to kill normal cells or autologous cells infected with EBV. Importantly, when the cytotoxic activity of tumor lysate pulsed DC-stimulated CD8+ T cells from POLE mutated vs. POLE wild type cancer patients was compared, the CTLs were found to be similarly effective in inducing killing of the autologous tumor targets (mean cytotoxicity±SEM: 43.4±7.3% versus 33.1±5.1% in POLE mutated vs POLE wild type (P=0.305) (FIG. 17).

TABLE 8

Patient characteristics and molecular features of tumors.

| Sample ID | Histology | Grade | Stage | Age | Race | Somatic missense POLE mutations | PBL | Tumor culture |
|---|---|---|---|---|---|---|---|---|
| FF40 | USC | G3 | IB | 57 | W | V411L-Y470H-S928I-F1099S-F1672L | yes | yes |
| FF9 | USC | G3 | IIIC | 56 | W | R77C-V411L-R742C-T1052M-V1452A | yes | no |
| UTE4 | Endometrioid | G3 | IVA | 65 | W | A957V | yes | yes |
| ARK6 | USC | G3 | IB | 48 | W | H76N-D368Y-A832T-C1642Y-A1967B-G2076V-L2207I | yes | yes |
| UTE9 | Endometrioid | G1 | IA | 43 | O | A456G | yes | no |
| ARK1 | USC | G3 | IVA | 62 | B | not present | yes | yes |
| ARK2 | USC | G3 | IVB | 63 | B | not present | yes | yes |
| FF16 | USC | G3 | IIIC | 54 | W | not present | yes | no |
| FF6 | USC | G3 | IA | 63 | B | not present | yes | no |
| ARK15N | USC | G3 | IIIC | 67 | W | not present | yes | yes |

Example 9

Figure 18:
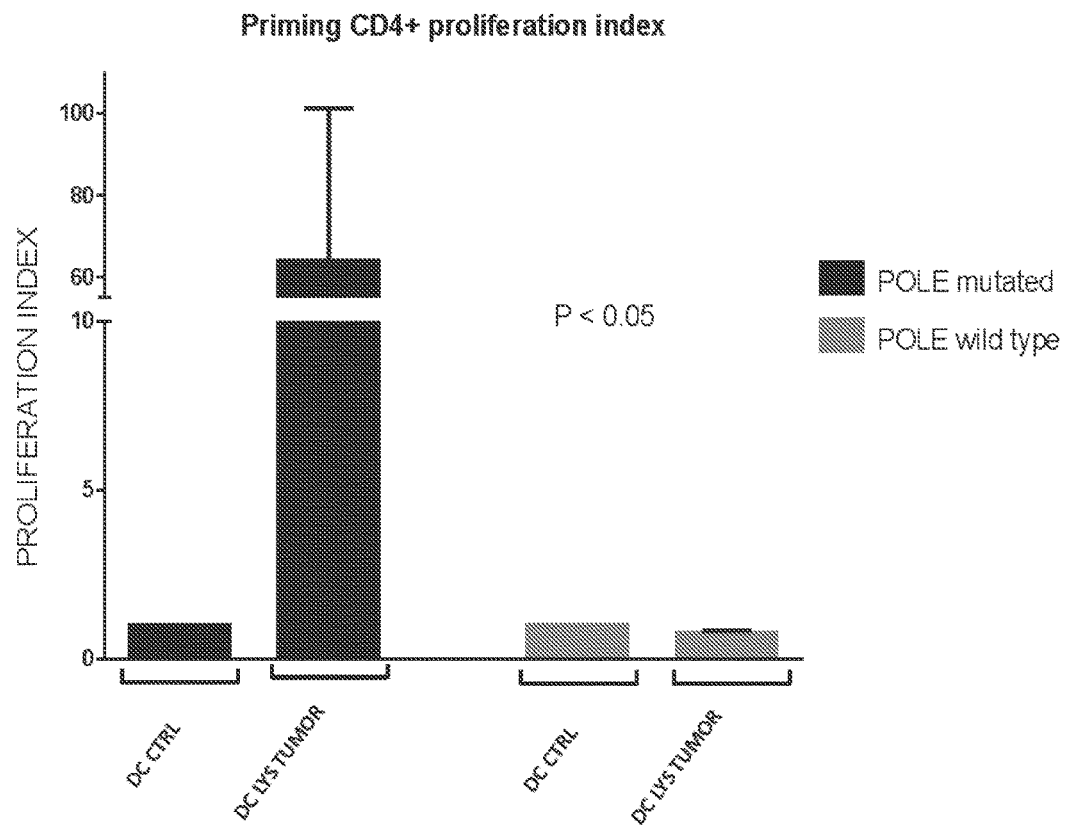
FIG. 18. is a histogram that illustrates tumor specific CD4+ T proliferation induced by tumor lysate-pulsed DCs in POLE mutated vs POLE wild type endometrial cancer patients in vitro, measured in CFSE based-assays after 72 hrs. Data are presented as mean proliferation index (±standard deviation) of CD4+ T cell-stimulated with tumor lysate-pulsed DCs vs PHA-activated peripheral blood lymphocytes lysate pulsed control DCs for the two groups of endometrial cancer patients. Proliferation assays were conducted after a minimum of two in vitro stimulation with tumor lysate-pulsed DC as described in the methods section.

Tumor-Specific Proliferations of CD4+ T Cells from POLE Mutated Vs POLE Wild Type Cancer Patients Tumor lysate-pulsed DC stimulated CD4+ T cells (purity >99%) from POLE (+) and POLE (−) cancer patients were tested for specific proliferation against tumor-lysate pulsed autologous DC or LCL. As controls, PHA-activated peripheral blood lymphocytes lysate pulsed autologous DC or LCL or autologous unpulsed DC or LCL were used. Proliferation assays were conducted after a minimum of two in vitro stimulations with tumor lysate-pulsed DC as described in the methods section. As shown in FIG. 18, consistent proliferations of autologous CD4+ T cells were detectable only after stimulation with DC pulsed with tumor lysate derived from POLE (+) endometrial cancer patients but not POLE (−) cancer patients. Indeed, only in POLE mutated cancer patients CD4+ T cell proliferations were significantly higher than those induced in CD4+ T cells stimulated by DC controls (FIG. 18, $P<0.05$).

Example 10

Tumor-Specific Proliferations of Naïve CD8+ and CD4+ T Cells from PBL.

Figure 19:
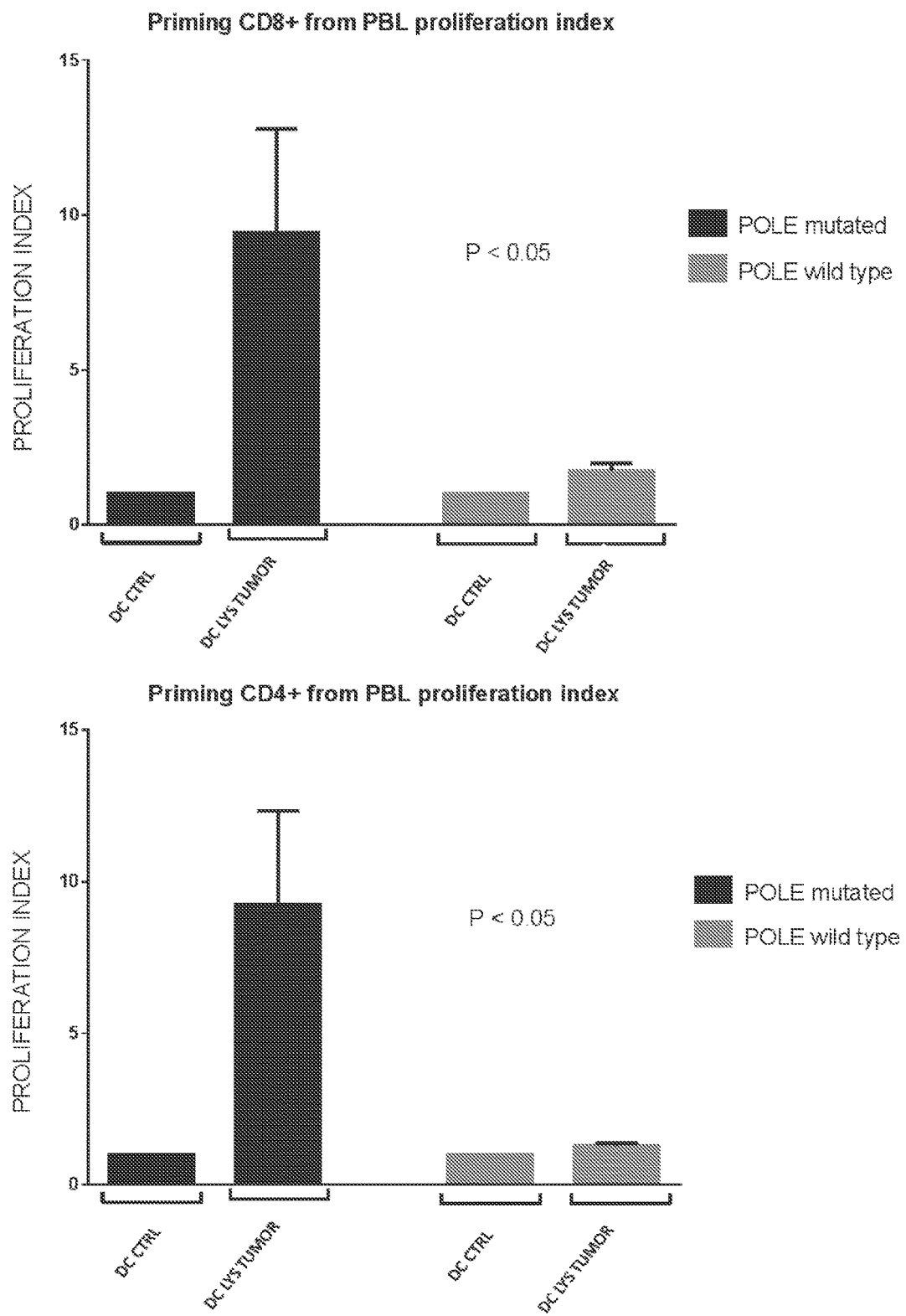
FIG. 19. is a series of histograms that illustrates tumor specific peripheral blood CD8+ and CD4+ T proliferations induced by tumor lysate-pulsed DCs in naïve (i.e., fresh PBL) obtained from POLE mutated vs POLE wild type endometrial cancers, measured by CFSE based-assays after 5 days. Data are presented as mean proliferation index (±standard deviation) of CD8+ and CD4+ T cells stimulated with tumor lysate-pulsed DCs vs PHA-activated peripheral blood lymphocytes lysate pulsed control DCs for the two groups of endometrial cancer patients.

In additional experiments, freshly collected (i.e., naïve) PBL from POLE (+) and POLE (−) cancer patients were evaluated for their ability to proliferate when cultured with tumor-lysate pulsed autologous DC in vitro. As controls, PHA-activated peripheral blood lymphocytes lysate pulsed autologous DC or LCL or autologous unpulsed DC or LCL were used. As clearly depicted in FIG. 19, a significant proliferation of both CD4+ and CD8+ freshly collected T cells from autologous PBL was detected only after stimulation with DC pulsed with tumor lysate derived from POLE (+) endometrial tumors but not POLE (−) cancer patients. Indeed, as shown in FIG. 19, only in this group of patients such proliferations were significantly higher than those induced in CD8+ and CD4+ T cells by PHA-activated peripheral blood lymphocytes lysate pulsed autologous DC or LCL alone or unpulsed DC controls ($P<0.05$).

Example 11

Intracellular Cytokine Expression by Tumor-Specific CD4+ T Cells

Figure 20:
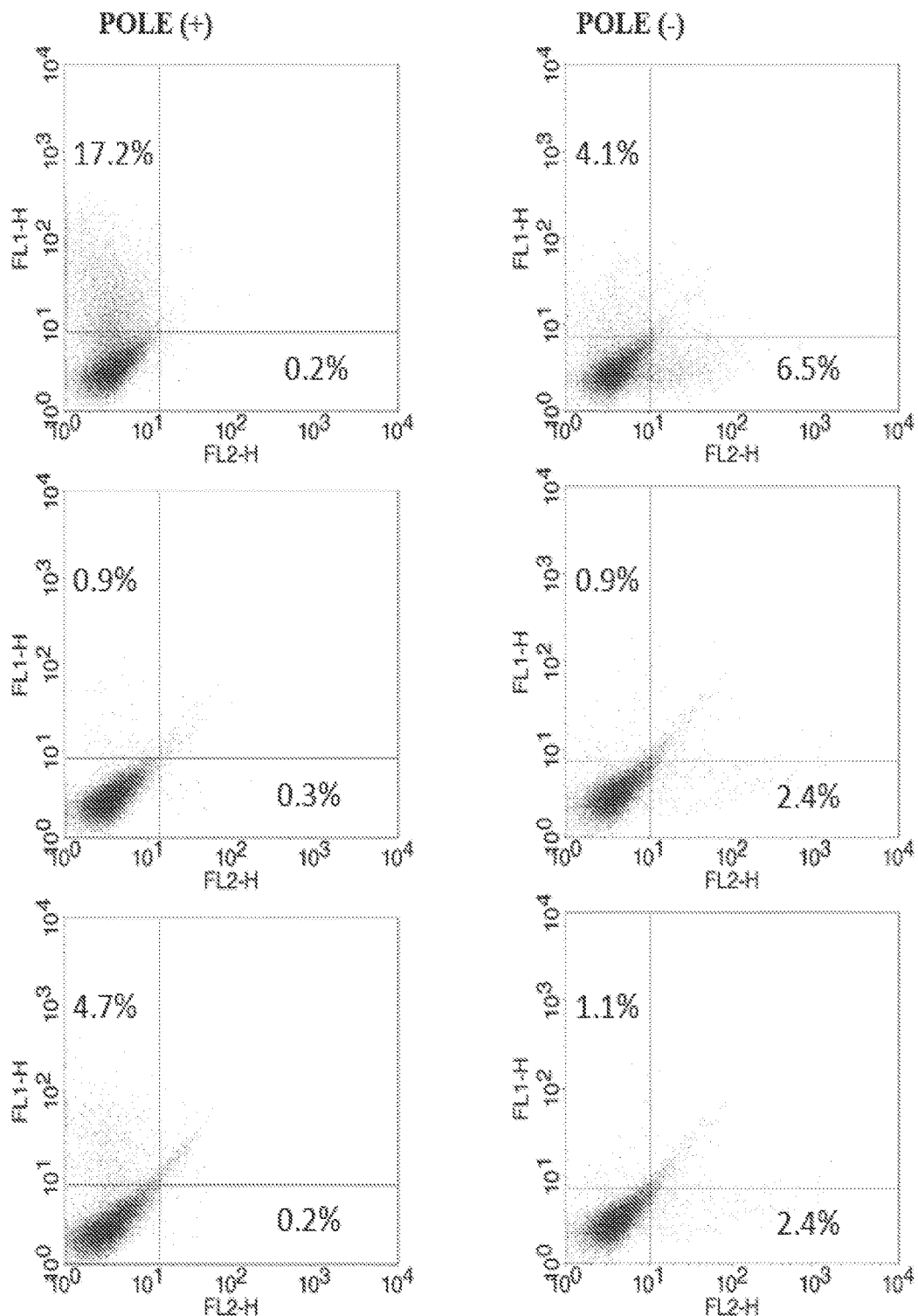
FIG. 20 is a series of graphs representing a two-color flow cytometric analysis of intracellular IFN-γ and IL-4 expression by tumor specific CD4+ T cells after overnight re-stimulation by tumor lysate-pulsed DC vs control DC pulsed with lysate from normal PBL in the presence of Brefeldin A. CD4+ T cells stimulated with OKT3 were used as positive control. A representative experiment using CD4+ T cells from a POLE mutated vs POLE wild type endometrial cancer patient is shown. Assays were conducted after a minimum of two in vitro stimulation with tumor lysate-pulsed DC as described in Methods. Upper panel: OKT3-restimulated CD4+ T cells. Middle Panel: control PBL-pulsed DC-restimulated CD4+ T cells. Lower Panel: control Tumor-pulsed DC-restimulated CD4+ T cells.

To evaluate whether cytokine expression from tumor-lysate stimulated CD4+ T cells from POLE (+) and POLE (−) cancer patients segregated in discrete IFN-γ+/IL-4− and IFN-γ−/IL-4+ subsets, flow cytometric techniques were used for the detection of intracellular cytokine expression at the single cell level. Two color flow cytometric analyses of intracellular IFN-γ and IL-4 expression by CD4+ T were performed after at least 6 weeks of culture. This was completed after overnight stimulation with tumor-lysate pulsed or unpulsed DC in the presence of Brefeldin A, as described in the methods section. As representatively shown in FIG. 4, only CD4+ T cells from POLE (+) mutated patients were found to express detectable amounts of intracellular IFN-γ after overnight stimulation with DC-loaded with POLE mutated tumor lysate ($P<0.05$). Consistently, among the populations of CD4+ T cells in these patients, more IFN-γ expressors than IL-4 secretors were found (FIG. 20). Importantly, DC pulsed with lysate from autologous control PBL or fibroblast or unpulsed DC controls stimulated only minimal IFN-γ expression in CD4+ T cells from POLE mutated patients after overnight stimulation (FIG. 20).

Example 12

The present invention, The Cancer Genome Atlas (TCGA) Network (Nature. 497:67-73, (2013)) and others (Bielas et al., Proc. Natl. Acad. Sci. USA 103, 18238-18242 (2006); Albertson et al., 106(40):17101-4, (2009); Briggs, S., and Tomlinson, I. The Journal of pathology 230, 148-153 (2013); Church et al., Human molecular genetics 22, 2820-2828 (2013); Palles et al., Nature genetics 45, 136-144 (2013); Zhao et al., Proc Natl Acad Sci USA 110(8):2916-21 (2013)) have recently shown that 7-10% of sporadic endometrial carcinoma may harbor somatic mutations in the proofreading exonuclease domain of DNA polymerase epsilon (POLE), the leading strand replicase. Polymerase proofreading is vital to ensure replication fidelity, and in keeping with this, cancers with POLE exonuclease mutations display striking levels of mutations (i.e., ultramutator phenotype). Importantly, recent reports in both Type I and Type II endometrial cancer patients have provided strong evidence that patients harboring tumors with POLE exonuclease-mutations may experience a significantly better prognosis when compared to the remaining group of endometrial cancer patients The basis of improved outcome in POLE ultramutated cancers is currently poorly understood. However, multiple non-mutually exclusive hypothesis have been used to explain the favorable prognosis of POLE mutated endometrial cancer patients. First, these tumors may be less fit than other cancers, possibly as a result of their extremely high number of mutations, to quickly spread and metastasize in the body. Second, because of their defective DNA repair, they may be more sensitive to standard anti-cancer treatments such as chemotherapy or radiation therapy. Finally, due to their extraordinary number of somatic mutations these cancers may be highly immunogenic for the host due to the large number of mutated epitopes.

Dendritic cells (DC) are the most potent antigen presenting cells known in humans and play a crucial role during the priming and reactivation of antigen specific immune responses (Banchereau et al., Nature. 392: 245-52 (1998)). This unique function as well as the recent standardization of DC culture conditions in vitro has provided the opportunity to evaluate their potential for the immunological treatment of cancer patients. Accordingly, using tumor-lysate pulsed autologous DC-activated lymphocytes, the present invention relates to an evaluation of the intrinsic immunogenicity of POLE mutated versus POLE wild type endometrial cancers using completely autologous human cancer models. This invention presents herein the first evidence that while both POLE+ and POLE– endometrial cancers could elicit significant cytotoxic T cell responses in vitro against autologous tumors, only the POLE ultra-mutated are able to consistently induce strong proliferation in both naïve and tumor specific CD4+ and CD8+ T cells. Furthermore, only POLE mutated tumor-lysate pulsed autologous DC were able to induce significant IFN-γ cytokine secretion and a Type I cytokine bias in proliferating CD4+ T lymphocytes from endometrial cancer patients. Taken together, these findings may, in part, explain the better prognosis of this subset of endometrial cancer patients (Zhao et al., Proc Natl Acad Sci USA 110(8):2916-21 (2013); Meng et al., Gyn. Onc. 134: 15-19 (2014); Hussein et al., Mod Pathol. (2014)) and therefore have important implications for the treatment of human tumors harboring POLE driver mutations.

Generation of potent CTL immune responses, in particular against weak antigens such as tumor-specific antigens (which are normally encountered outside an inflammatory context), requires the presence of CD4 helper T cells and the presence of both helper and CTL determinants on the same APC 9 Bennett et al., J. Exp. Med. 186: 65-70 (1997); Ossendorp et al., J. Exp. Med. 187: 5, 693-702 (1998); Lanzavecchia. Nature 393, 413-414 (1998)). Indeed, the inability to mount a potent antitumor immune response against tumors has often been attributed to the lack of generation of sufficient tumor-specific T cell help. Consistent with this view, in clinical studies, the in vivo persistence of adoptively transferred antigen specific CD8+ T cells against cytomegalovirus (Vitiello et al., 95: 341-349 (1995)), or the enhanced generation of hepatitis B specific CTLs (Walter et al., N. Engl. J. Med. 333: 1038-1044 (1995)) was dependent upon endogenous CD4 responses. Moreover, the generation of tumor reactive T helper cells has been shown to be particularly important for the immunotherapy of established (i.e., vascularized) tumors and metastatic disease in several murine tumor models (Pulask et al. Cancer Res. 58: 1486-1493 (1998); Baskar et al. J. Exp. Med. 181: 619-629 (1998)). Accordingly, the in vitro experimental results presented herein suggest that POLE ultra-mutated tumors may trigger strong immunity in vivo because of the combined activation of both the helper and the cytotoxic arms of the immune system.

POLE proofreading-mutant endometrial cancers are ultra-mutated, with a base substitution mutation frequency among the highest found in human tumors (i.e., the number of somatic mutations in these tumors exceed by far those found in micro-satellite instable (MSI) endometrial and colorectal mutated cancers). Importantly, a high load of somatic mutations has been recently associated with a survival benefit from immune checkpoint abrogation in human tumors (Snyder et al., N Engl J Med 371:2189-2199 (2014)). The data presented herein, including the fact that POLE mutated tumors display prominent immune infiltrate in vivo, suggests that POLE ultra-mutated tumors, similar to melanoma and lung cancer patients with high mutation burden, may strongly benefit from the use of novel immunotherapeutic approaches based on blocking immune check-points antibodies (i.e., anti-CTLA4-ipilimumab, anti-PD1-nivolumab, Bristol Meyers Squibb, NY, N.Y.).

The present invention provides the first evidence that POLE ultra-mutated tumors may be significantly more immunogenic when compared to POLE (–) endometrial tumors, in particular to the helper arm of the immune system.

The disclosures of each and every patent, patent application, and publication cited herein are hereby incorporated herein by reference in their entirety.

While the invention has been disclosed with reference to specific embodiments, it is apparent that others skilled in the art may devise other embodiments and variations of this invention without departing from the true spirit and scope of the invention. The appended claims are intended to be construed to include all such embodiments and equivalent variations.

What is claimed is:

1. A method of treating a mammal with a cancerous tumor, wherein the method comprises:
   i. sequencing the nucleotide sequence of DNA polymerase epsilon (POLE) gene from a sample isolated from the mammal's cancerous tumor;
   ii. comparing the nucleotide sequence of the POLE gene from the sample isolated from the mammal's cancerous tumor and the corresponding nucleotide sequence from a control sample,
   iii. detecting one or more mutations in the POLE gene from the mammal's cancerous tumor indicating that the mammal carries a high mutator phenotype; and,
   iv. administering to the mammal, at least one treatment selected from the group consisting of Ipilimumab and autologous-monocyte derived dendritic cells loaded with cancer cell lysate.

2. The method of claim 1, wherein the mutation in POLE from the mammal's cancerous tumor includes at least one base mutation selected from the group consisting of a base deletion, base insertion, base duplication, and base substitution.

3. The method of claim 2, wherein the base mutation generates a synonymous or non-synonymous change in the corresponding protein or enzyme.

4. The method of claim 3, wherein the protein or enzyme associated with the base mutation has distinct activity from the protein or enzyme from a control sample.

5. The method of claim 1, wherein the cancerous tumor is a cancer selected from the group consisting of lung, colon, breast, prostate, endometrial, ovarian, melanoma, kidney, liver, and lymphoma.

6. The method of claim 1, wherein the detection of a high mutator phenotype in the mammal's cancerous tumor is indicative of a high immunogenicity in the mammal.

7. The method of claim 1, further comprising administering to the mammal an additional treatment selected from the group consisting of a chemotherapeutic treatment, an anti-cell proliferating treatment and any combination thereof.

8. The method of claim 1, wherein the mammal is a human.

* * * * *